US008463361B2

(12) United States Patent
Tupin, Jr.

(10) Patent No.: US 8,463,361 B2
(45) Date of Patent: Jun. 11, 2013

(54) SYSTEM AND METHOD FOR NON-INVASIVE INSTANTANEOUS AND CONTINUOUS MEASUREMENT OF CARDIAC CHAMBER VOLUME

(75) Inventor: Joe Paul Tupin, Jr., Truckee, CA (US)

(73) Assignee: LifeWave, Inc., Los Altos, CA (US)

( * ) Notice: Subject to any disclaimer, the term of this patent is extended or adjusted under 35 U.S.C. 154(b) by 403 days.

(21) Appl. No.: 12/601,665

(22) PCT Filed: May 23, 2008

(86) PCT No.: PCT/US2008/064760
§ 371 (c)(1),
(2), (4) Date: Nov. 24, 2009

(87) PCT Pub. No.: WO2008/148040
PCT Pub. Date: Dec. 4, 2008

(65) Prior Publication Data
US 2010/0179421 A1    Jul. 15, 2010

Related U.S. Application Data

(60) Provisional application No. 60/939,855, filed on May 24, 2007.

(51) Int. Cl.
*A61B 5/00*    (2006.01)
(52) U.S. Cl.
USPC ........... 600/427; 600/407; 600/410; 600/411; 600/424; 600/425; 600/429; 600/430; 600/437; 600/438; 606/130
(58) Field of Classification Search
USPC ................. 600/407, 410, 411, 424, 425, 427, 600/429, 430, 437, 438; 606/130
See application file for complete search history.

(56) References Cited

U.S. PATENT DOCUMENTS

| 4,373,527 A | 2/1983 | Fischell |
| 4,848,354 A | 7/1989 | Angelsen et al. |

(Continued)

FOREIGN PATENT DOCUMENTS

| WO | WO01/70103 A2 | 9/2001 |
| WO | WO2007/027660 A2 | 3/2007 |

(Continued)

OTHER PUBLICATIONS

Tupin, Jr. et al.; U.S. Appl. No. 12/765,680 entitled "Fetal Monitoring Device and Methods," filed Apr. 22, 2010.

(Continued)

*Primary Examiner* — Brian Casler
*Assistant Examiner* — Amanda Lauritzen
(74) *Attorney, Agent, or Firm* — Shay Glenn LLP

(57) ABSTRACT

A system and method for non-invasive and continuous measurement of cardiac chamber volume and derivative parameters including stroke volume, cardiac output and ejection fraction comprising an ultrawideband radar system having a transmitting and receiving antenna for applying ultrawideband radio signals to a target area of a subject's anatomy wherein the receiving antenna collects and transmits signal returns from the target area which are then delivered to a data processing unit, such as an integrated processor or PDA, having software and hardware used to process the signal returns to produce a value for cardiac stroke volume and changes in cardiac stroke volume supporting multiple diagnostic requirements for emergency response and medical personnel whether located in the battlefield, at a disaster site or at a hospital or other treatment facility.

19 Claims, 36 Drawing Sheets

U.S. PATENT DOCUMENTS

| | | | |
|---|---|---|---|
| 4,901,725 A | 2/1990 | Nappholz et al. | |
| 5,036,248 A | 7/1991 | McEwan et al. | |
| 5,088,498 A | 2/1992 | Beach et al. | |
| 5,097,837 A | 3/1992 | Reuschel | |
| 5,257,627 A | 11/1993 | Rapoport | |
| 5,274,271 A | 12/1993 | McEwan | |
| 5,292,348 A | 3/1994 | Saumarez et al. | |
| 5,345,471 A * | 9/1994 | McEwan | 375/130 |
| 5,361,070 A | 11/1994 | McEwan | |
| 5,457,394 A | 10/1995 | McEwan | |
| 5,465,094 A | 11/1995 | McEwan | |
| 5,510,800 A | 4/1996 | McEwan | |
| 5,511,553 A | 4/1996 | Segalowitz | |
| 5,512,834 A | 4/1996 | McEwan | |
| 5,517,198 A | 5/1996 | McEwan | |
| 5,519,400 A | 5/1996 | McEwan | |
| 5,521,600 A | 5/1996 | McEwan | |
| 5,523,760 A | 6/1996 | McEwan | |
| 5,540,733 A | 7/1996 | Testerman et al. | |
| 5,560,363 A | 10/1996 | Torp et al. | |
| 5,563,605 A | 10/1996 | McEwan | |
| 5,573,012 A | 11/1996 | McEwan | |
| 5,576,627 A | 11/1996 | McEwan | |
| 5,581,256 A | 12/1996 | McEwan | |
| 5,589,838 A | 12/1996 | McEwan | |
| 5,609,059 A | 3/1997 | McEwan | |
| 5,610,611 A | 3/1997 | McEwan | |
| 5,630,216 A | 5/1997 | McEwan | |
| 5,661,385 A | 8/1997 | McEwan | |
| 5,662,115 A | 9/1997 | Torp et al. | |
| 5,682,164 A | 10/1997 | McEwan | |
| 5,736,958 A | 4/1998 | Turpin | |
| 5,738,102 A | 4/1998 | Lemelson | |
| 5,754,144 A | 5/1998 | McEwan | |
| 5,757,320 A | 5/1998 | McEwan | |
| 5,758,652 A | 6/1998 | Nikolic | |
| 5,766,208 A * | 6/1998 | McEwan | 600/595 |
| 5,767,953 A | 6/1998 | McEwan | |
| 5,774,091 A | 6/1998 | McEwan | |
| 5,805,110 A | 9/1998 | McEwan | |
| 5,820,561 A | 10/1998 | Olstad et al. | |
| 5,832,772 A | 11/1998 | McEwan | |
| 5,883,591 A | 3/1999 | McEwan | |
| 5,980,463 A | 11/1999 | Brockway et al. | |
| 6,031,421 A | 2/2000 | McEwan | |
| 6,126,611 A | 10/2000 | Bourgeois et al. | |
| 6,213,947 B1 | 4/2001 | Phillips | |
| 6,233,479 B1 | 5/2001 | Haddad et al. | |
| 6,292,433 B1 | 9/2001 | Gilbert et al. | |
| 6,325,761 B1 | 12/2001 | Jay | |
| 6,348,898 B1 | 2/2002 | Rosenbury et al. | |
| 6,373,428 B1 | 4/2002 | McEwan | |
| 6,414,627 B1 | 7/2002 | McEwan | |
| 6,454,711 B1 | 9/2002 | Haddad et al. | |
| 6,454,719 B1 | 9/2002 | Greenhut | |
| 6,471,689 B1 | 10/2002 | Joseph et al. | |
| 6,491,639 B1 | 12/2002 | Turcott | |
| 6,535,161 B1 | 3/2003 | McEwan | |
| 6,676,608 B1 | 1/2004 | Keren | |
| 6,738,044 B2 | 5/2004 | Holzrichter et al. | |
| 6,829,378 B2 | 12/2004 | DiFilippo et al. | |
| 6,899,684 B2 | 5/2005 | Mault et al. | |
| 6,914,552 B1 | 7/2005 | McEwan | |
| 6,944,107 B2 | 9/2005 | Fukushima et al. | |
| 6,984,207 B1 | 1/2006 | Sullivan et al. | |
| 7,003,348 B1 | 2/2006 | Brewer et al. | |
| 7,025,729 B2 | 4/2006 | de Chazal et al. | |
| 7,075,485 B2 | 7/2006 | Song et al. | |
| 7,224,944 B2 | 5/2007 | McEwan | |
| 7,294,105 B1 | 11/2007 | Islam | |
| 7,304,580 B2 | 12/2007 | Sullivan et al. | |
| 7,305,052 B2 | 12/2007 | Spiridon et al. | |
| 7,432,847 B2 | 10/2008 | Fedotov et al. | |
| 7,652,581 B2 | 1/2010 | Gentry et al. | |
| 7,654,962 B2 | 2/2010 | Sullivan | |
| 7,725,150 B2 * | 5/2010 | Tupin et al. | 600/407 |
| 2003/0088180 A1 | 5/2003 | Van Veen et al. | |
| 2003/0090407 A1 | 5/2003 | Santhoff | |
| 2004/0100376 A1 | 5/2004 | Lye et al. | |
| 2004/0111045 A1 | 6/2004 | Sullivan et al. | |
| 2004/0249257 A1 | 12/2004 | Tupin, Jr. et al. | |
| 2005/0101841 A9 | 5/2005 | Kaylor et al. | |
| 2006/0094937 A1 | 5/2006 | Immoreev et al. | |
| 2006/0154642 A1 | 7/2006 | Scannell, Jr. | |
| 2006/0200033 A1 | 9/2006 | Keren et al. | |
| 2006/0274031 A1 | 12/2006 | Yuen et al. | |
| 2007/0027367 A1 | 2/2007 | Oliver et al. | |
| 2007/0055164 A1 | 3/2007 | Huang et al. | |
| 2007/0135866 A1 | 6/2007 | Baker et al. | |
| 2007/0156031 A1 | 7/2007 | Sullivan et al. | |
| 2007/0276270 A1 | 11/2007 | Tran | |
| 2008/0001735 A1 | 1/2008 | Tran | |
| 2008/0004904 A1 | 1/2008 | Tran | |
| 2008/0009685 A1 | 1/2008 | Kim et al. | |
| 2008/0027337 A1 | 1/2008 | Dugan et al. | |
| 2008/0058740 A1 | 3/2008 | Sullivan et al. | |
| 2008/0119896 A1 | 5/2008 | Wong et al. | |
| 2008/0129511 A1 | 6/2008 | Yuen et al. | |
| 2008/0146938 A1 | 6/2008 | Hazard et al. | |
| 2008/0169931 A1 | 7/2008 | Gentry et al. | |
| 2008/0243431 A1 | 10/2008 | Wai | |
| 2008/0294019 A1 | 11/2008 | Tran | |
| 2009/0048500 A1 | 2/2009 | Corn | |
| 2009/0054737 A1 | 2/2009 | Magar et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076401 A1 | 3/2009 | Mazar et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0203972 A1 | 8/2009 | Heneghan et al. | |
| 2009/0227882 A1 | 9/2009 | Foo | |
| 2011/0060215 A1 * | 3/2011 | Tupin et al. | 600/425 |
| 2012/0041281 A1 | 2/2012 | Tupin, Jr. et al. | |
| 2012/0059268 A1 | 3/2012 | Tupin, Jr. | |

FOREIGN PATENT DOCUMENTS

| | | |
|---|---|---|
| WO | WO2007/101343 A1 | 9/2007 |
| WO | WO2007/120904 A2 | 10/2007 |
| WO | WO2007/124126 A2 | 11/2007 |
| WO | WO2007/143535 A2 | 12/2007 |
| WO | WO2008/057883 A2 | 5/2008 |
| WO | WO2009/029453 A2 | 3/2009 |
| WO | WO2009/036256 A1 | 3/2009 |
| WO | WO2009/036306 A1 | 3/2009 |
| WO | WO2009/036313 A1 | 3/2009 |

OTHER PUBLICATIONS

Tupin, Jr. et al.; U.S. Appl. No. 12/759,909 entitled "System and Method for Extracting Physiological Data Using Ultra-Wideband Radar and Improved Signal Processing Techniques," filed Apr. 14, 2010.

Tupin, Jr. et al.; U.S. Appl. No. 12/749,861 entitled "Apparatus and Method for Continuous Noninvasive Measurement of Respiratory Function and Events," filed Mar. 30, 2010.

McKee et al.; The natural history of congestive heart failure: the Framingham study; N. Engl. J. Med.; vol. 285; No. 26; pp. 1441-1446; Dec. 23, 1971.

Neubauer, Stefan; The failing heart—an engine out of fuel; N. Engl. J. Med.; vol. 356; No. 11; pp. 1140-1151; Mar. 15, 2007.

* cited by examiner

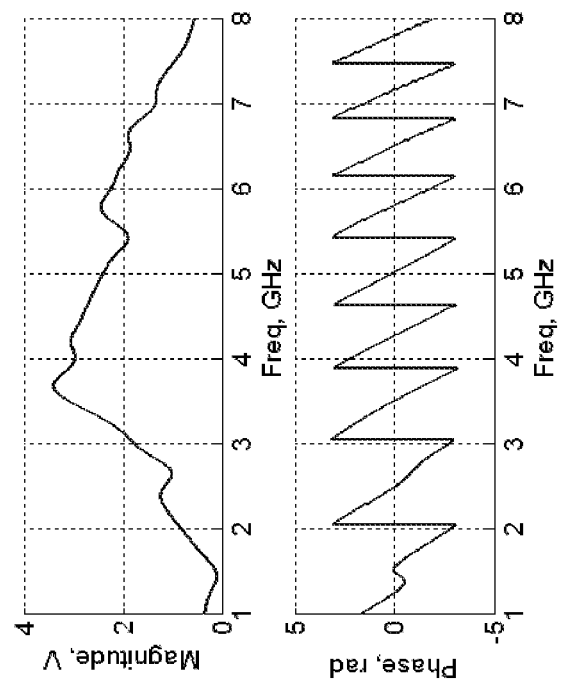
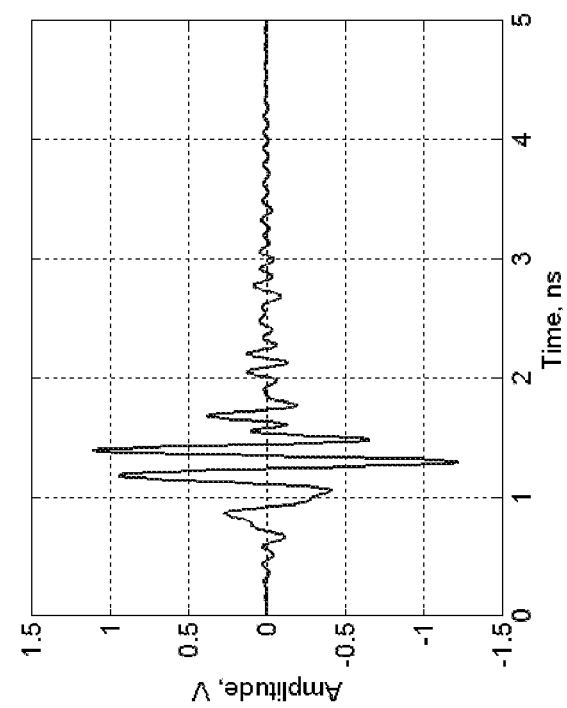
FIG. 8b
FIG. 8a

SYSTEM AND METHOD FOR NON-INVASIVE INSTANTANEOUS AND CONTINUOUS MEASUREMENT OF CARDIAC CHAMBER VOLUME

CROSS REFERENCE TO RELATED APPLICATIONS

Priority is claimed to U.S. Provisional Application No. 60/939,855 filed May 24, 2007, titled "SYSTEM AND METHOD FOR NON-INVASIVE INSTANTANEOUS AND CONTINUOUS MEASUREMENT OF CARDIAC CHAMBER VOLUME" which is referred to and incorporated herein in its entirety by this reference.

TECHNICAL FIELD

The present invention relates in general to cardiac monitoring. More particularly, the present invention relates to a system and method for non-invasive physiological monitoring to determine cardiac spatial changes and associated cardiac functionality.

BACKGROUND ART

A large number of medical conditions can directly affect the heart including heart failure, abnormal blood pressure, pregnancy, and trauma. Cardiac data can provide information on the progression of a disease or injury affecting a patient. The ability to safely, easily, and accurately measure cardiac function will provide the healthcare professional with critical information needed to provide appropriate and timely care. A system that enables a reliable measurement of cardiac data is therefore critical in the provision of effective health care. Both qualitative and quantitative aspects of cardiac function need to be monitored to assess, diagnose and treat problematic cardiac symptoms. In particular, stroke volume, cardiac output, and ejection fraction are important parameters commonly measured to aid a physician in determining a patient's state of cardiac health and uncover other conditions that might affect cardiac health.

Definition of Key Cardiac Functional Metrics:

Stroke volume is defined as the amount of blood pumped by the left ventricle of the heart in one contraction. Stroke volume is calculated by subtracting the left ventricle diastolic volume from the left ventricle systolic volume. The heart does not pump all the blood out of the ventricle with each contraction. In healthy individuals, only about two-thirds of the blood in the ventricle is displaced and pumped out with each heartbeat. For example, if the left ventricle diastolic volume is 125 ml and the left ventricle systolic volume is 55 ml, the stroke volume is 70 ml.

Cardiac output is defined as the volume of blood pumped by the heart over a fixed period of time. Typically, cardiac output is expressed as the volume of blood pumped by the left ventricle in one minute. Cardiac output is calculated by multiplying the stroke volume by the heart rate. For example, if there are 70 beats per minute and 70 ml of blood is ejected with each beat of the heart, the cardiac output is 4900 ml/minute. This value is typical for an average adult at rest, although cardiac output may reach up to 30 liters/minute during extreme exercise.

Ejection fraction is defined as the ratio of the volume of blood pumped by the heart with respect to the maximum volume of the heart. Specifically, ejection fraction is calculated by dividing the left ventricle stroke volume by the left ventricle diastolic volume. For example, if 70 ml of blood is ejected with each beat of the heart and the diastolic LV volume is 125 ml, the corresponding ejection fraction is 56%. Ejection fraction provides a measure of the heart's pumping efficiency with ratios in the 50% to 60% range being normal for healthy adults while ratios below 35% are an indicator of serious cardiovascular problems.

Examples of Medical Conditions Affecting Cardiac Function:

Heart failure is a disorder in which the heart pumps blood inadequately, leading to reduced blood flow, back up and congestion of blood in the veins and lungs, and other changes that may further weaken the heart, eventually leading to death. Changes in cardiac function associated with heart failure result in a decrease in cardiac output. Decreased cardiac output is caused by a decline in stroke volume that is due to systolic dysfunction, diastolic dysfunction, or a combination of the two. Systolic dysfunction results from a loss of intrinsic inotropy or contractility, most likely due to alterations in signal transduction mechanisms responsible for regulating inotropy. Global systolic dysfunction can also result from the loss of viable, contracting muscle as occurs following acute myocardial infarction. Diastolic dysfunction refers to the diastolic properties of the ventricle and occurs when the ventricle becomes less compliant or stiffer, which impairs ventricular filling. Both systolic and diastolic dysfunctions produce a higher ventricular end-diastolic pressure, which serves as a compensatory mechanism to augment stroke volume according to the Frank-Starling mechanism. The Frank-Starling mechanism describes the ability of the heart to change its force of contraction and therefore stroke volume in response to changes in venous return. In some types of heart failure, such as dilated cardiomyopathy, the ventricle dilates as preload pressures increase to recruit the Frank-Starling mechanism in an attempt to maintain normal stroke volumes.

High blood pressure is another negative medical condition related to poor cardiac function. High blood pressure with no known cause is called primary or essential hypertension. Estimates suggest between 85% and 90% of people with high blood pressure have primary hypertension. Several factors, including changes in the heart and blood vessels probably combine to increase blood pressure. For instance, cardiac output may be increased and the resistance to blood flow may be increased because blood vessels are constricted, causing higher blood pressure. Additionally, a subject's blood volume may also be increased which will also increase blood pressure. The reasons for such changes are not fully understood but appear to involve an inherited abnormality affecting the constriction of arterioles, which help control blood pressure.

Contrarily, low blood pressure is another negative condition related to poor cardiac function. Various disorders and drugs can result in low blood pressure. For example, cardiac output may be reduced as a result of heart disease, such as a heart attack (myocardial infarction), a heart valve disorder, an extremely rapid heartbeat (tachycardia), a very slow heartbeat (bradycardia), or other abnormal heart rhythm (arrhythmia).

Cardiac function during pregnancy is an important indicator of both fetal and maternal health. During pregnancy, the mother's heart must work harder because as the fetus grows, the heart must pump more blood to the uterus. By the end of pregnancy, the uterus is receiving approximately one-fifth of the mother's blood supply. During pregnancy, the mother's cardiac output increases by 30 to 50%. As cardiac output increases, the mother's resting heart rate speeds up from a normal pre-pregnancy rate of about 70 beats per minute to 80 or 90 beats per minute. During exercise, cardiac output and heart rate increase more when a woman is pregnant than when she is not. During labor, cardiac output increases by an additional 10%. After delivery, cardiac output decreases rapidly at first, then more slowly, returning to the mother's pre-pregnancy level about six weeks after delivery. Various complications during pregnancy manifest themselves through changes in cardiac function. For example, cardiac output is significantly elevated in a preclinical state of pre-eclampsia, a serious condition exhibited by an attack of convulsions that can lead to coma, seizures, and death. Consequently, the capability to track a mother's and her fetus's cardiac function during pregnancy can provide critical information to enhance care and outcomes.

Cardiac functional measurement is a critical parameter to track in many circumstances, including emergency situations. For example, hemorrhage, profuse and uncontrollable bleeding, is the primary cause of death on the battlefield and a leading cause of death in civilian trauma. Under conditions of hemorrhage, the stimuli for cardiovascular compensation are similar: both decrease venous return and preload, resulting in both decreased stroke volume and cardiac output. The reduction of stroke volume during hemorrhage reflects the degree of blood loss, but accurate assessment of stroke volume during emergency situations in the field is currently not possible. Hence, it would be beneficial if emergency response personnel were provided with portable devices to track stroke volume.

Current Diagnostic Techniques:

The need for reliable real-time, non-invasive monitoring and measurement of stroke volume, cardiac output, and ejection fraction is considerable. Current devices and techniques suffer from several serious limitations, including but not limited to: extreme and risky invasive application, the need for direct attachment of devices to the subject, complicated operation and/or interpretation allowing only skilled individuals to effectively use the devices, exposure to exceptionally hazardous ionizing radiation, large and bulky systems which prevent mobility and flexible utility in field settings, and, among others, defeat by physical barriers. These drawbacks greatly limit their applicability to, at best, controlled clinical settings, depriving the overall population of important medical information. Effective, mobile systems that can easily be used by a responder are not available.

Following are brief descriptions of current devices and techniques used to monitor cardiac function. One of the most frequently used, an electrocardiogram, generally known as an ECG or EKG, is a test that records the heart's electrical activity using electrodes attached to the surface of the chest. Cardiac data is obtained by measuring the surface electrical signals emanating from the conductive cells of the heart during the cardiac cycle. Measurement of the electrical signals transmitted by the cardiac nerves and propagated through the heart muscle provides an indirect indication, rather than a direct indication, of the mechanical function of the heart. A significant problem associated with an ECG is that electrical signals do not necessarily give a direct indication of the heart's actual pumping status. For example, electrical signals can still be measured and reported by an ECG device when the heart is actually in mechanical standstill and no blood is flowing. This false positive, pulse less electrically activity, can obviously lead to confusion for the caregiver or emergency responder, potentially causing inappropriate treatment.

Merely sensing that the heart is beating electrically still may not provide sufficient information to determine whether the left and right ventricles are actually contracting, and thus outputting blood, Further, using traditional ECG-based methods, it can be difficult to determine whether each of the ventricles are in fact contracting in unison and thereby evenly distributing blood. The ability to monitor the mechanical motion of the ventricles would provide significant additional information to accurately assess cardiac function.

Echocardiography is a second technology commonly used to collect cardiac data. It involves the use of low power, high frequency ultrasound waves, which are directed at the heart by placing a transducer covered in conductive gel directly on the surface of the chest and aiming the transducer at the heart. Echocardiography is generally suitable only for single batch measurement and cannot be easily adapted for continuous or instantaneous monitoring. Echocardiography can be used to obtain limited two-dimensional imaging of the left ventricle to provide estimates of cardiac chamber volume, which in turn allow rough calculation of estimated ejection fraction, stroke volume and cardiac output. Another echocardiography technique uses Doppler ultrasound to measure cardiac output. Echocardiographic measurement of the aortic root cross-sectional area (or, alternatively, the descending aorta area) is multiplied by the Doppler measured velocity-time integral of blood flow through that area combined with the heart rate to yield cardiac output. Again, these echocardiography techniques provide single measurements and cannot be easily adapted for continuous or instantaneous monitoring.

Echocardiography has other practical limitations. The ultrasound-imaging machines used in echocardiography are bulky, power hungry, expensive, and technically complex. They also require a skilled sonographer to hold and manipulate the gel-covered transducer while simultaneously optimizing settings. Additionally, ultrasound waves do not propagate well through either bone, such as the ribs or sternum, or air, resident in lungs, which can create an acoustic impediment to tracking heart motion. In fact, some patients cannot be ultrasonically imaged because of poor acoustic windows. Because of these limitations, echocardiography is typically limited to intermittent use in a hospital or clinical environment and has never been know to be used as a continuous, mobile long-term monitoring technique.

In addition to the above, various forms of cardiac catheterization may be used to assess a subject's cardiac health. However, cardiac catheterization is an extremely invasive, risky and expensive procedure. Catheterization actually requires the insertion of different sensors in the cardiac chambers. Due to its extremely invasive nature, cardiac catheterization can introduce a wide range of complications, including bleeding at the puncture site, cardiac arrhythmia, cardiac tamponade, vein or artery trauma, low blood pressure, infection, embolism from blood clots, allergic reaction, hemorrhage, stroke or death. Although cardiac catheterization can provide useful information concerning cardiovascular function, the associated risks posed make it undesirable for many patients. In fact, cardiac catheterization, in and of itself, can be a significant contributor to subject morbidity.

A first catheter-based method used to determine stroke volume is the "direct" Fick cardiac output technique. This technique is based on the principle that the difference in oxygen content across the lungs multiplied by the measured cardiac output should equal the total amount of oxygen transferred into the blood each minute. First, this approach requires the accurate measurement of the subject's total oxygen uptake from a bag, which the patient breathes from during the course of the test. Next, determining the oxygen difference across the lungs also requires obtaining invasive blood samples from the patient's systemic arteries and from the patient's vena cava or pulmonary arteries. These measurements require multiple medical personnel performing meticulous measurements and invasive sampling for a single snapshot determination of stroke volume. Multiple or serial determinations are not feasible.

A second catheter-based technique for obtaining cardiac data is the "indirect" Fick cardiac output method. Since the collection and accurate analysis of a large bag of expired gas is difficult, as required in the "direct" Fick methodology, the "indirect" Fick relies on an assumption of the average expected oxygen consumption. However, the indirect Fick still requires invasive sampling of arterial and venous blood with catheters to obtain the arterial venous oxygen difference. In addition, the assumption of oxygen consumption is very likely to introduce error in the final calculation of cardiac output. Additionally, as with the "direct" Fick method, given the need for significant personnel and lab requirements, this technique is only used in cardiac catheterization and research laboratories.

A third catheter-based technique is the indicator dilution method. In this approach, one injects a known amount of dye or thermal fluid into a subject's flowing blood stream. The dilution of the agent downstream from its injection point may be used as a measure of the volume that produced the dilution per unit of time. Again, as with other undesirable catheter approaches, this technique also requires invasive catheter access to both the central venous and arterial systems, with all its associated potential complications.

Indicator dilution methods using dyes are rarely performed today. Instead, modern approaches rely on thermal dilution techniques. Catheters are fitted with a distal heated filament, which allows automatic thermo-dilution measurement via heating the blood and measuring the resultant thermo-dilution trace. Due to associated negative impacts, dilution measurements cannot be performed too frequently, and, can be subject to error in the presence of certain muscle relaxants. The thermal dilution technique is currently used in catheterization laboratories and can be used to obtain serial measurements of cardiac output in patients with pulmonary artery catheters in acute care settings. However, as with other cardiac catheterization techniques, the invasive catheter requires trained personnel for placement and repeated injections. Although monitoring for days is possible, longer periods are associated with catheter related infections and other complications.

Impedance cardiography (ICG), also known as thoracic electrical bio-impedance, is an additional technology used to assess cardiac function. ICG works in conjunction with ECG, which creates a more complex application. ICG is based on associating measured changes in thoracic impedance to estimates of changes in thoracic volume. As with an ECG, ICG can only be used to indirectly track volumetric changes during the cardiac cycle. In practice, with an ICG, an alternating current is transmitted through a subject's chest. The current is expected to seek the path of least resistance, which is generally presumed to be the blood-filled aorta. However, other features such as lung congestion can affect this measurement. Baseline thoracic impedance to the impressed current is measured and then, the corresponding changes in impedance are used in conjunction with ECG to provide hemodynamic parameters. The technique requires careful placement of four neck and four chest electrodes, along with trained personnel and additional specialized equipment.

Generally, the type of cardiac monitoring used, whether intermittent or continuous, has been found to affect delivery of care. In a study of patients with low cardiac output states in a coronary care unit, cardiac output determined by using a continuous method was compared with cardiac output determined by using an intermittent method every 4 hours. It was shown that the method used to monitor cardiac output delivered data that directly affected delivery of care. Continuous measurement of cardiac output increased the number of treatment decisions and actions by healthcare providers and decreased the length of hospital stay by a median of 2 days.

An ideal system for measuring stroke volume and cardiac output would combine the best qualities of the previously described existing systems without the associated negative aspects. It would be desirable to provide a cardiac measuring system that can detect advanced cardiac functions, but is not invasive, does not require surgery, preferably does not even require any skin contact, conductive gels or electrode patches, is low power without any significant ionizing radiation, allows long-term continuous patient monitoring, is extremely safe, and is much more affordable than current techniques. The present invention is directed to overcoming, or at least reducing, the effects of one or more of the problems set forth above.

DISCLOSURE OF INVENTION

Technical Problem

A device does not exist in the medical industry which is capable of noninvasively and continuously measuring changes in cardiac chamber volume in a subject. The need for reliable real-time, non-invasive monitoring and measurement of stroke volume, cardiac output, and ejection fraction is considerable. Current devices and techniques suffer from several serious limitations, including but not limited to: extreme and risky invasive application, the need for direct attachment of devices to the subject, complicated operation and/or interpretation allowing only skilled individuals to effectively use the devices, exposure to exceptionally hazardous ionizing radiation, large and bulky systems which prevent mobility and flexible utility in field settings, and, among others, defeat by physical barriers. These drawbacks greatly limit their applicability to, at best, controlled clinical settings, depriving the overall population of important medical information. Effective, mobile systems that can easily be used by a responder are not available.

Technical Solution

A system and method for non-invasive instantaneous and continuous measurement of cardiac chamber volume is described herein. In particular, a non-invasive system and method for determining dynamic and structural physiologic data from a living subject including a change in the spatial configuration of a subject's heart to assist in determining overall cardiac health comprising an ultrawideband radar system having a transmitting and receiving antenna for applying ultrawideband radio signals to a target area of the subject's anatomy wherein the receiving antenna collects returns from the target area which are then delivered to a data processing unit, such as an integrated processor, a PDA or Personal Computer, having software and hardware used to process the signal returns to produce a value for cardiac stroke volume and changes in cardiac stroke volume supporting multiple diagnostic requirements for both mobile patients with chronic heart conditions and in support of emergency response and medical personnel whether located in the battlefield, at a disaster site or at a hospital or other treatment facility.

In one aspect of the present invention, an ultrawideband sensor is provided to collect direct mechanical data concerning the subject's cardiac status, which is received by a processing unit capable of resolving a change in a spatial configuration of the subject's heart.

In another aspect of the present invention, a medical device is provided that includes a control unit, an antenna, and a sensing unit capable of resolving a change in a spatial configuration of a beating heart.

In yet another aspect of the present invention, a method is provided that includes receiving a reflected signal originally transmitted from outside a subject's body and directed at the subject's heart and determining a change in a dimension of the heart, due to the heart beating, based upon the transmitted and reflected signal.

The present invention, LifeWave's Ultrawideband Medical Radar (UWBMR) is an active imaging technology composed of two primary parts, an ultrawideband (UWB) radar transceiver and a signal processor, which integrates hardware and software elements in conjunction with a CPU to measure, track and display cardiac function and associated functional parameters. The UWBMR transceiver in one configuration is based on a low-PRF (pulse repetition frequency) transmitter and a swept-range receiver where the transmitter generates a series of UWB pulses and the receiver captures the resulting reflections across a target range of interest, such as across a patient's chest cavity, including one or more cardiac chambers. In another configuration, the transmitter comprises an impulse transmitter. The signal processor operates on the range-dependent reflections to extract desired data, including instantaneous cardiac chamber volume and its derivatives—stroke volume, cardiac output, and ejection fraction.

In practice, the UWBMR transceiver transmits a series of extremely short duration electromagnetic pulses into the human body. As the energy enters the body and encounters a boundary between different biological substances such as skin-fat or muscle-blood, small amounts of the incident energy are reflected back towards the UWBMR where they are captured and pre-processed by the receiver.

The receiver captures the raw reflections using a high speed sample and hold circuit where the desired capture time for the sampler is set equal to the round trip time of flight from the transmitter to the target or range of interest and back to the receiver.

A number of sampled reflections from a given depth or range are integrated to minimize high frequency noise that corrupts the desired data related to tracking instantaneous cardiac volume. The integrated signal is amplified and passed through a low-pass filter to prevent signal aliasing prior to digitization.

After a predetermined number of reflections for a first range of interest are collected and integrated, the receiver sample timing is changed, allowing capture of reflections from the next range of interest. This process is repeated until reflections from the entire range of interest, such as across the cardiac chamber or chest, are collected and then the process is continually repeated to deliver an updated instantaneous measure of cardiac volumetric changes.

For dynamic structures like the heart, the physical location of the boundaries within the target range of interest will move with respect to the transceiver's antenna, producing a complex series of time-varying reflections. The time-varying reflections are continually processed by the signal processor to extract information on the activity of the heart, particularly mechanical activity.

According to the present invention, for calculation of the instantaneous cardiac chamber volume, the digitized radar reflections are first range aligned on sweep boundaries and passed through a series of high pass filters to minimize low frequency noise and static clutter, such as reflections from inanimate objects like bone. The resultant data associated with all anatomical motion in the range of interest, including cardiac and pulmonary motion, is then amplified and coarse quantized using a binary quantizer where the quantizer threshold for a given sweep or row is based on the median value of the data set, resulting in an intermediate black and white image. Depending on the specific anatomical motion selected for monitoring, other statistical portions of the data set may be selected for image creation. After creation of the initial image, a speckle filter is then applied to the image to remove random speckle noise and increase the sharpness of the image boundary edges, supporting accurate determinate of spatial change. For example, a speckle filter having a 3×3 kernel may be applied, but other speckle filters could be applied depending on the desired sharpness of the boundary edges, which would influence the accuracy of the assessment of spatial change.

Once the filtering steps are completed, the data is successfully presented as an image space full of various spatial structures changing in time that represent both heart wall motion and various noise sources including organs, bones, patient motion, and stray radiofrequency (RF) emissions. To further refine the collected and processed data, four additional metrics are developed and integrated as part of the method of the invention to delineate and confirm that the structures found in the image space are, in fact, cardiac wall excursions and not caused by other signal sources.

A first metric developed and integrated within the signal-processing module to support determination of instantaneous cardiac volume (the "ICV" module) is the cardiac rate, which is detected via application and processing of the UWBMR signals. The ICV module determines the cardiac rate via conversion of the entire swept image space to a predetermined frequency domain using a Fast Fourier Transform (FFT) algorithm that identifies and isolates the image region (range bin) of the swept range containing the strongest cardiac signal. Uniquely, while confirming the cardiac rate, the methodology also provides the range of depth containing the targeted cardiac motion, which is critical to the development and assessment of additional important ICV module metrics.

A second metric developed and integrated within the ICV module is the identification and verification of the completeness of the target cardiac structure as it changes over time. As the heart muscle behaves in a sustained and rhythmic fashion, the ICV module identifies those signals that qualify for further analysis by capturing and prioritizing those signals with respect to minimum discontinuities. The algorithmic process associated with the ICV module leverages a chain coding technique in conjunction with structural morphological techniques to minimize signal discontinuities caused by noise loss, such as white noise.

A third metric of the ICV module is the continual and repeated identification and tracking of an ellipsoid characteristic in the candidate image space that best characterizes the approximate motion of the anterior and posterior cardiac walls through time. A corollary, yet opposite, component of this third metric is the isolation and avoidance of signals having a non-ellipsoid characteristic; these non-ellipsoid signals indicate the likely presence of a non-cardiac signal source.

A fourth metric of the ICV module is the development of a correlation between the time-domain characteristics of the isolated cardiac range bin identified by the first cardiac rate metric with points identified in the image space that represent minimum, maximum, and zero-crossing points of cardiac wall excursions in the image space as identified by the second and third metrics, structure completeness and ellipsoid characteristics.

Image regions that meet the requirements of the above metrics are isolated and identified as good candidates for further analysis with the final candidate selected as providing the truest representation of instantaneous cardiac volume as the candidate having the strongest characteristics in all metrics.

As a final, repetitive step in the ICV module, with the current final candidate chosen, the minimum and maximum cardiac wall excursions are identified and quantified using the prior data acquired and already available from the assessment of the four key metrics. The minimum and maximum cardiac wall excursions then allow the actual chamber wall displacement to be calculated by counting the spatial pixels traversed from a min-point to a max-point of the cardiac waveform and multiplying the number of pixels by the resolution of the data acquisition device (DAQ).

Instantaneous cardiac volume may then be determined by calculating from the wall excursion distances based upon presumed dimensions of the heart chamber. The heart chamber can be represented by a number of different shapes depending on the accuracy desired. For example, the chamber can be presumed to be in the shape of a simplified sphere, or alternatively, a more representative asymmetric changing ellipsoid. So, in a first approach, instantaneous cardiac volume is calculated using the equation to derive the volume of a simple sphere. The ICV module of the present invention is adaptive to include more complex volumetric calculation models based upon a more complete physical model of the targeted cardiac chamber, including a model based on more complex static imaging, such as from an MRI.

With heart rate and instantaneous chamber volume data produced via the present invention, the present invention then also produces an instantaneous and continual display of the various derivative and parallel cardiac performance parameters. These parameters include but are not limited to stroke volume, cardiac output, and ejection fraction. Stroke volume is calculated by taking the difference between the maximum and minimum chamber volume on a beat-by-beat basis. Cardiac output is calculated by multiplying the stroke volume by the heart rate. Ejection fraction is calculated by dividing the stroke volume by the diastolic chamber volume.

Advantageous Effects

The present invention allows a caregiver to easily monitor a patient's cardiac status without invasive techniques. The invention can measure heart rate and instantaneous chamber volume to produce an instantaneous and continual display of derivative cardiac performance parameters. These parameters include but are not limited to stroke volume, cardiac output, and ejection fraction.

BRIEF DESCRIPTION OF DRAWINGS

For fuller understanding of the present invention, reference is made to the accompanying drawings numbered below. Where reference numbers are provided, commonly used reference numbers identify the same or equivalent parts of the claimed invention throughout the several figures.

The invention may be understood by reference to the following description taken in conjunction with the accompanying drawings, in which the leftmost significant digit(s) in the reference numerals denote(s) the first drawing in which the respective reference numerals appear, and in which:

FIG. 8a illustrates the received reflections for the test case with the heart included as viewed in the time domain, according to the present invention and using the Bow-tie antenna.

FIG. 8b illustrates the corresponding magnitude and phase of the frequency spectrum for the received signal of the test case without a heart, according to the present invention.

Figure 1:
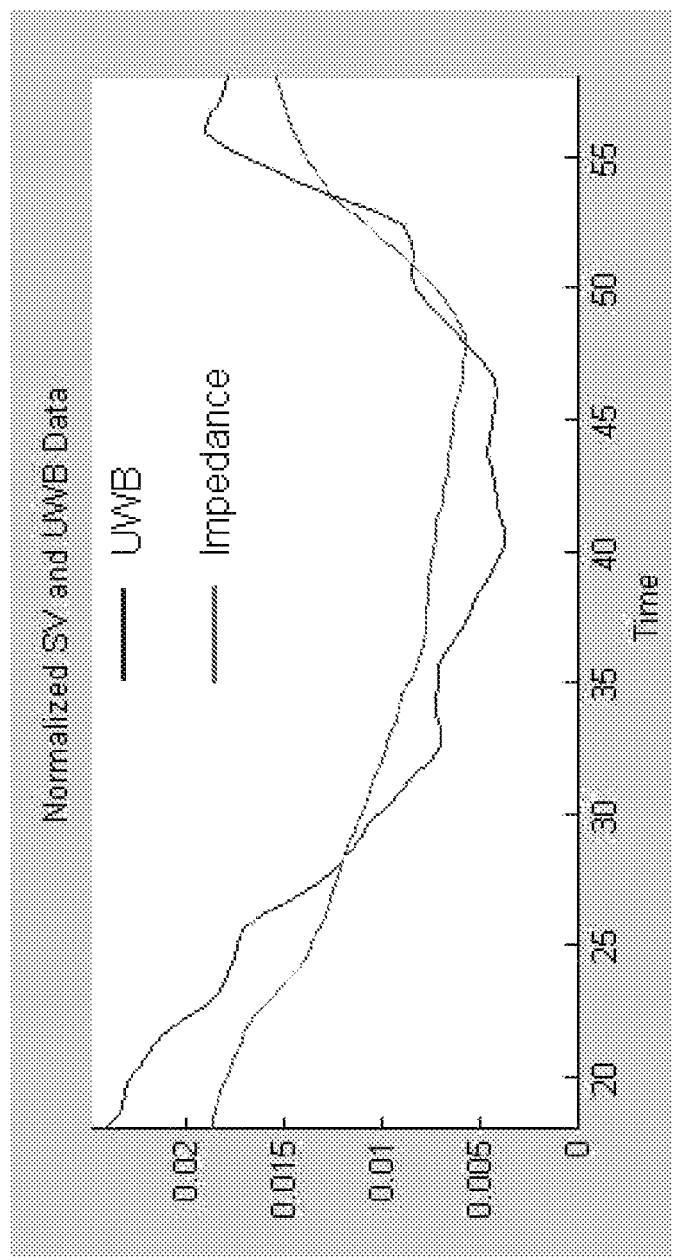
FIG. 1 is an illustrative graph showing the measured change in cardiac stroke volume during hypovolemia, according to the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

BEST MODE FOR CARRYING OUT THE INVENTION

The present invention is the result of a novel multi-step data collection and analysis process involving both computer simulations and empirical testing using a prototype ultrawideband medical radar (UWBMR) device with a unique single chamber mechanical phantom as well as animal models. The simulations required the creation and novel interrelation of anatomical models, antenna models, and transmitted radar waveform models. The subsequent computer simulation of cardiac displacement measurement employed the previously developed models in a variety of configurations. Analysis of the computer simulations provided new and novel results that supported development of a novel medical imaging system based upon ultrawideband signals.

The present invention includes a unique single chamber cardiac phantom created to simulate ventricle cardiac activity to support empirical testing of the UWBMR to establish accuracy, identify, and test various novel algorithmic elements for incorporation in software used to process the data delivered by the UWBMR to determine instantaneous stroke volume and other derivative cardiac metrics. The cardiac phantom serves to provide certain baseline information necessary to create the software systems for signal processing and production of a display of changes in cardiac chamber volume.

Referring now to FIG. 1, an illustration of the measurements of stroke volume from the present invention juxtaposed against an invasive impedance measurement technique is provided. The accuracy of the stroke volume measurements from the UWBMR was substantiated via collection of empirical data from animal testing. Although other configurations are possible, one approach and configuration comprises incorporation of the UWBMR with a hand-held computing and display device, such as a Personal Digital Assistant (PDA) or a cell phone.

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Now, in greater detail, the systems and methods comprising the present invention are described.

Embodiments of the present invention provide for determining the function of a heart and, thus for assisting in determining problems and delivering solutions associated with the function of the heart. The present invention supports the provision of various responses by caregivers to modify the behavior of a subject's heart. For example, the present invention includes the delivery of a pacing and/or stimulation signal from an external or implantable medical device to a portion of the heart in response to an output from the UWBMR sensor indicating that one or more problems exist in the function of the heart. Additionally, the invention diagnostic output is used to drive and guide external manual stimulation of the heart by an inexperienced individual faced with an emergency situation. Still further, the present invention provides information as part of a treatment protocol to support a decision to initiate or make a change in medications to a subject to alter heart function. Moreover, still further, the present invention provides information supporting a decision to perform surgery on a subject to rectify a critical heart condition.

The present invention demonstrates a novel system and method using ultrawideband radar to detect conditions within the heart that may be assessed and aggregated to produce a measurement of changes in cardiac chamber volume. In particular, the present invention supports the instantaneous and continuous noninvasive measurement of changes in cardiac volume. The present invention processes reflected signals to determine and measure cardiac rate and rhythm. Further, the present invention provides an instantaneous assessment of stroke volume and other advanced cardiac parameters like cardiac output and ejection fraction. The present invention provides a unique capability to continuously and instantaneously monitor and track the cardiac chamber movement and metrics to provide critical information which directly supports assessment of the health of the heart and cardiovascular system. Current devices for detecting changes in chamber volume (respiratory gas analysis, bio-impedance, echocardiography, and catheter-based techniques) are impractical for home based monitoring, emergency medical teams or chaotic trauma care situations common to the battlefield. They are also impractical for widespread use in the clinical environment due to their inherent risk to the patient, complexity and cost.

The UWBMR system of the present invention applies novel methods to non-invasively extract medical and physiological data from subjects. The UWBMR is capable of accurately measuring cardiopulmonary function without requiring direct skin contact. The UWBMR comprises a miniature UWB radar transceiver connected to a data processing device, hosting software and signal processing components. The UWBMR system, in combination with proprietary algorithms included in the software and hardware components, produces a novel output that allows one to non-invasively detect and track heart and lung motion. In another embodiment with software modifications, the UWBMR system has demonstrated its ability to image small manmade objects embedded in a medium that mimics biological tissue.

The UWBMR system has been successfully used to collect cardiopulmonary rate and rhythm information for use in patient monitoring and to evaluate resuscitation efforts. In addition, further system optimizations and configurations have enabled collection of multidimensional images using synthetic aperture radar (SAR) techniques. The novel integration of these features of the UWBMR enables external, non-invasive measurement of cardiac stroke volume using a portable handheld detector that is inexpensive, accurate, and non-invasive.

The UWBMR utilizes electromagnetic energy to interrogate the body and extract physiological data. Finite Difference Time Domain (FDTD) analysis techniques are used to model the electromagnetic interaction between complex 3-dimensional physical systems such as the human body and radar antennas. The FDTD simulation protocol used, in conjunction with a cardiac phantom, to develop elements of the present invention is described in the following steps:

1. Creation of a 3-dimensional model of the heart and surrounding thoracic region that is representative of the human anatomical structure with associated complex electrical properties for the various tissue types.
2. Creation of a means to change chamber volume, e.g., cardiac phantom.
3. Creation of a 3-dimensional model of antenna structures used in the UWBMR.
4. Creation of a process for simulating ventricular chamber functionality, including starting from a chamber volume corresponding to normal diastole, stimulating the system model using a single cycle Gaussian pulse with zero mean as the excitation source; then repeating the simulations, decreasing the chamber volume in incremental steps until normal systole chamber volume is reached.
5. Creation of a novel software and hardware signal processing system to analyze the resultant data and determine algorithmic adjustments to accurately detect changes in stroke volume, including, comparing received reflections across a range of chamber volumes to quantify differences observed, and, correlation with ranges of the UWBMR receiver.

To support operation of the UWBMR, finite difference time domain (FDTD) models of the heart and chest were developed based on anatomic and complex dielectric data. Models were developed that represented a variety of heart sizes. These models provide a thorough representation of expected patient physiologies and encompass the expected standard anatomical variation in the adult population. The invention can incorporate other non-standard models specific to particular individuals or populations.

Figure 2B:
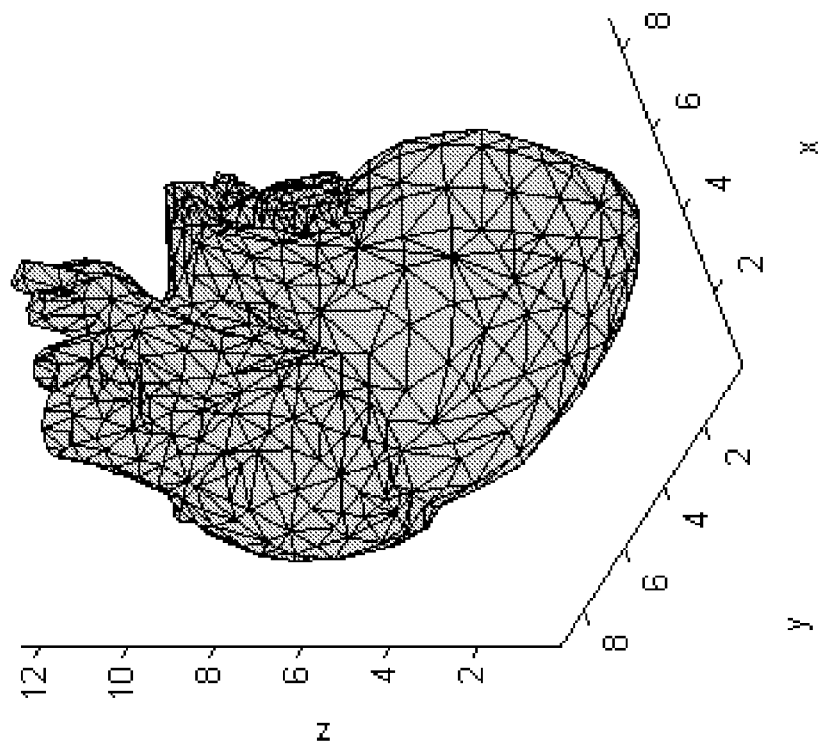
FIGS. 2a and 2b illustrate a 200 ml 3D mesh model and a 270 ml 3D mesh model developed to form the basis for measuring cardiac spatial changes, according to the present invention.
Figure 2A:
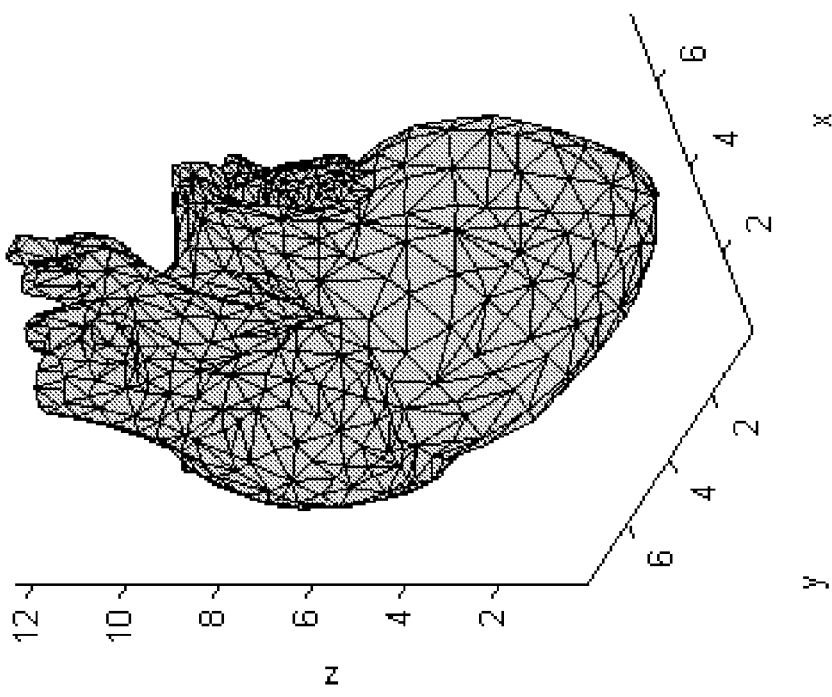

As illustrated in FIGS. 2a and 2b, the volumetric model integrated within the present invention was designed and configured to provide an accurate assessment of cardiac function. The volumetric model is comprised of a volumetric voxel mesh composed of a set of small cubic cells. In addition, the model includes association of complex electrical properties with each cell. The model further includes a unique implementation to support the UWBMR applications by identification and selection of a minimum mesh size for the model based on the shortest operational wavelength of the ultrawideband signal used to interrogate a target area of the heart. An important feature of the model, the minimum mesh size is determined using the following relationship:

$$\text{Mesh Size}_{minimum} = \frac{\lambda_{minimum}}{20\sqrt{\varepsilon r}}; \quad [\text{Eq. 1}]$$

where $$\lambda_{minimum} = \frac{c}{\text{Frequency}_{maximum}}$$

Where:
- $\varepsilon r$ is the relative dielectric constant of the medium through which the transmitted signal must propagate;
- c is the speed of light ($3 \times 10^{10}$ cm/sec)
- $\text{Frequency}_{maximum}$ is the highest frequency of interest in the transmitted signal in Hz;
- $\lambda_{minimum}$ is the corresponding shortest operational wavelength for the transmitted ultra-wideband signals measured in centimeters;
- 20 is the constant used to ensure the mesh size of the model will be significantly smaller than the minimum wavelength to ensure the mesh size is an accurate dimension for simulation purposes.

The three-dimensional structural model of the heart corresponds to specific UWBMR requirements to support application of multiple functional dynamic models of a beating human heart, based on nonlinear mesh deformation. Models representing total heart volumes ranging from 200 milliliters to 270 milliliters in 10-milliliter steps were integrated as components of the invention. In a first model, a 70 ml difference in left ventricle (LV) volume is equivalent to a 50% change in chamber volume based on a healthy adult male heart. As illustrated in FIGS. 2a and 2b, the present invention incorporates mesh configurations for a 200-milliliter model and a 270-milliliter model.

The model associated with the invention further includes a process for the interrelation of complex electrical properties for individual tissues and organs found in the human chest. Table 1, below, lists various anatomical structure and associated complex dielectric values used in the FDTD models associated with the invention.

TABLE 1

Complex Dielectric Constants for Various Human Structures

| Anatomical Structure | Epsilon ($\varepsilon$) | Sigma ($\sigma$) |
|---|---|---|
| Bone | 12.4 | 0.2 |
| Fat | 4.72 | 0.05 |
| Muscle | 60 | 1.32 |
| Skin | 39.9 | 0.72 |
| Lung | 20.5 | 0.42 |
| Heart | 57.48 | 1.22 |
| Trachea | 55.9 | 1.12 |
| Cerebra Spinal Fluid | 68.1 | 2.45 |
| Esophagus | 71.1 | 1.35 |

Based upon the variables described in Table 1, optimized antenna configurations are incorporated within the model of the present invention. These antenna configurations are best suited to providing desired signal transmissions and signal reflection reception to support calculation of actual cardiac chamber volume. The antenna design of the present invention is optimized to support application where the antenna is in close contact with high dielectric material and the direction of propagation is into the high dielectric material. In addition, we were able to identify key variables associated with increased directionality and show that increased directionality can be readily achieved but usually at the cost of increased antenna thickness.

Figure 3B:
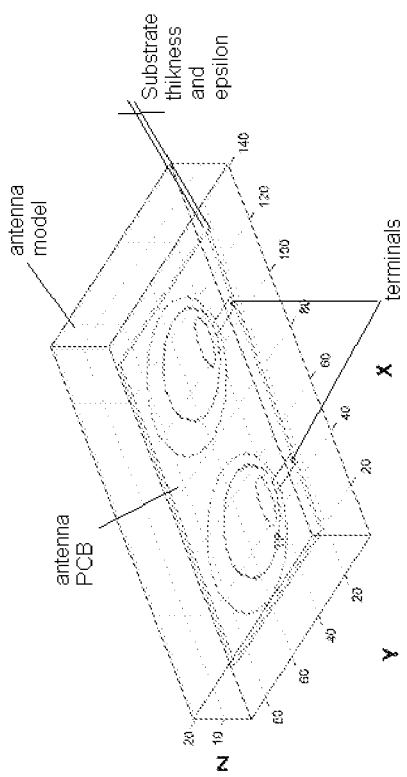
FIG. 3b is a model of an SEE antenna according to the present invention.
Figure 3A:
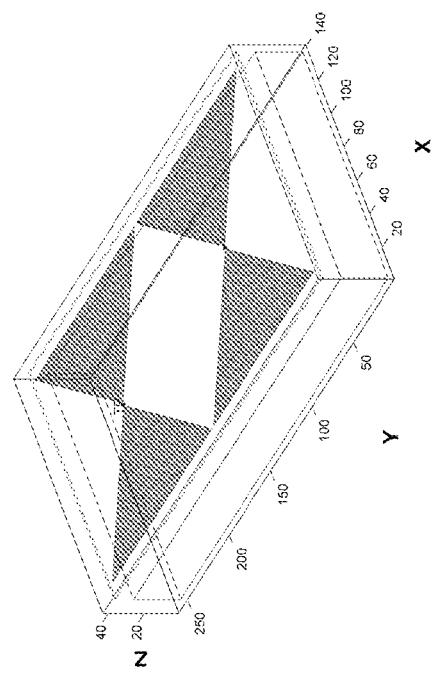
FIG. 3a is a model of a Bowtie antenna, according to the present invention.

Each model used for the present invention consists of two identical antennas—one for transmission of the UWBMR signal pulses and one for reception of reflected signals. As illustrated in FIG. 3a, in a first embodiment, the antennas are a Bowtie structure. As illustrated in FIG. 3b, in a second embodiment, a single element elliptical (SEE) structure is provided. Key antenna simulation parameters are listed in Table 2, below.

TABLE 2

Antenna Simulation Parameters

| Parameter | Bowtie Antenna | SEE Antenna |
|---|---|---|
| Frequency Range ($R_L > 10$ dB) | 1 GHz to 8 GHz | 3 GHz to 8 GHz |
| Physical Dimensions | 60 mm long × 60 mm wide | 57 mm long × 33 mm wide |
| Feed | Center | End |

Figure 4B:
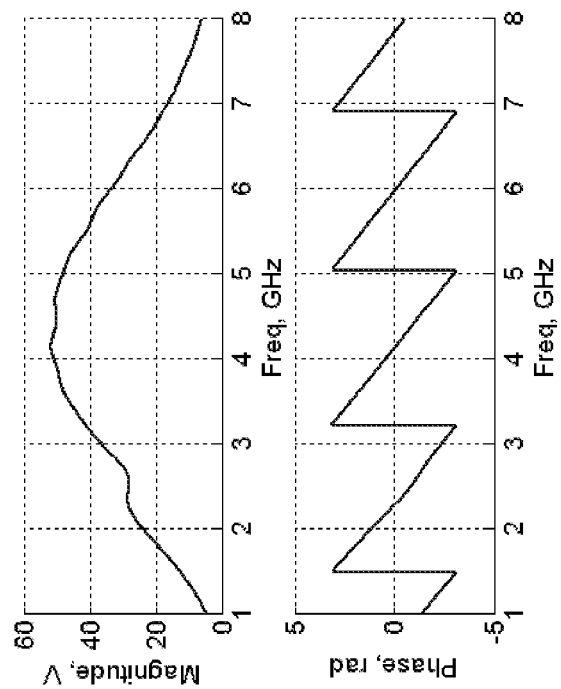
FIGS. 4a and 4b illustrate the amplitude and spectrum of a transmitted signal, according to an embodiment of the present invention.
Figure 4A:
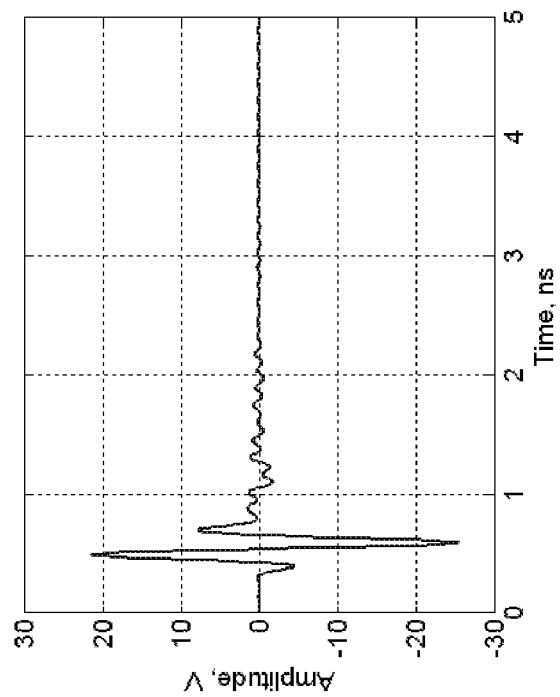

The model of the present invention further includes variable parameters that are modifiable to allow improved calibration. For example, two reference test cases using the bowtie antenna structure were used to refine and validate the FDTD anatomical model and collect information on the required receiver sensitivity and dynamic range. Both test cases used the same transmitted pulse shape. The pulse shape was chosen to produce a transmitted frequency spectrum that complies with the UWB medical frequency band as defined by the FCC in Rule & Order 02-48. FIG. 4a illustrates a transmitted pulse as viewed in the time domain while FIG. 4b illustrates the corresponding magnitude and phase of the pulse in the frequency domain.

Figure 5:
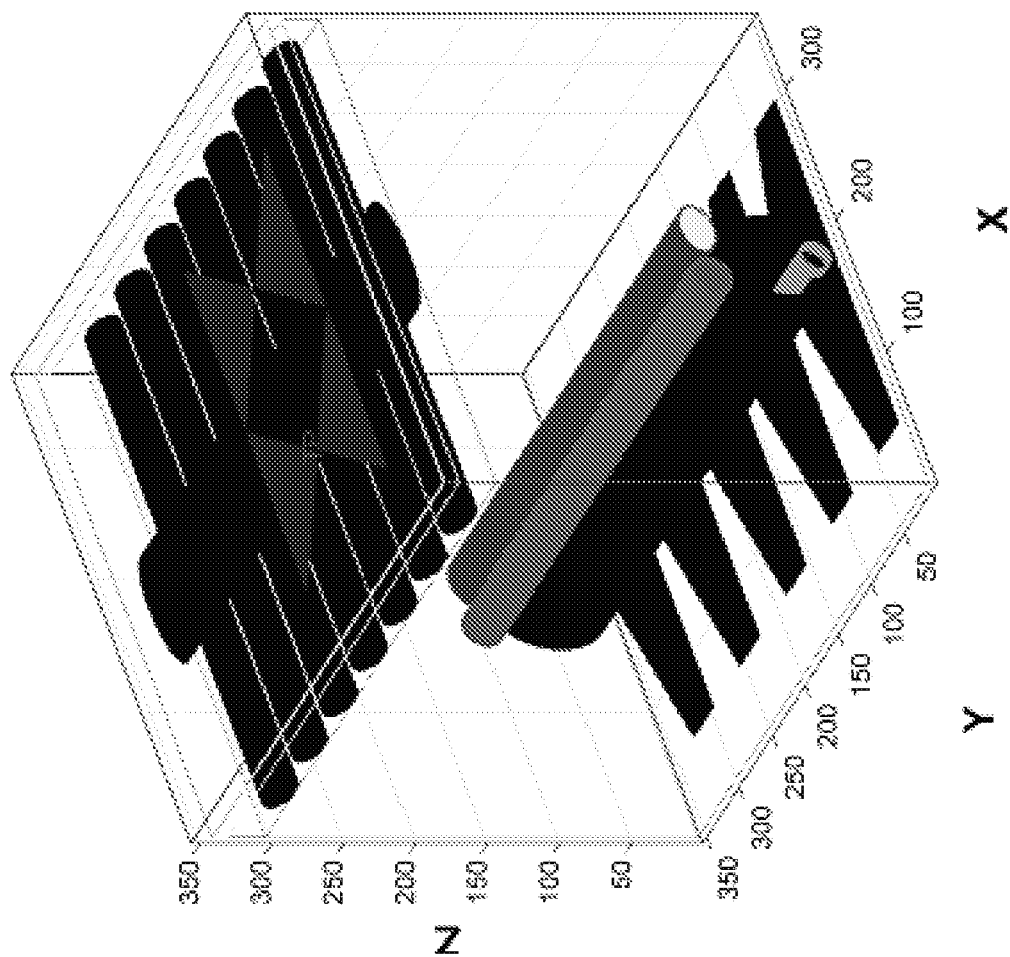
FIG. 5 illustrates an FDTD model without a heart used in the development and refinement of the spatial configuration process, according to the present invention.
Figure 7:
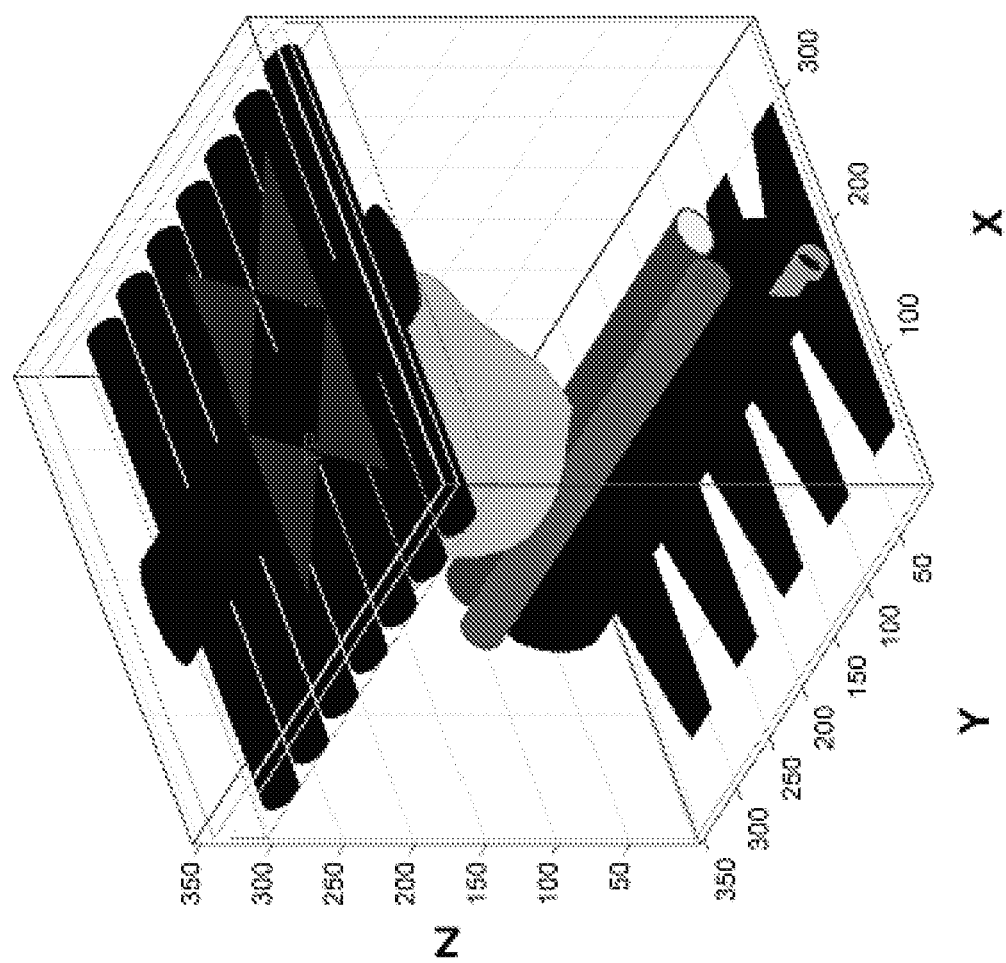
FIG. 7 illustrates an FDTD model with a heart used in the development and refinement of the spatial configuration process, according to the present invention.

The present invention supports the comparison or results from two tests to calibrate the model of the invention based on the yield of quantifiable differences in received signals. With reference to FIG. 5, a first test case excludes the heart from the anatomical model. With reference to FIG. 7, the heart is included in the anatomical model of the second test case.

Again, with reference to FIG. 5, the basic structure of the anatomical model of the present invention excluding the heart is illustrated. The lungs have also been omitted for clarity but were included in the actual model as tested. A pair of Bowtie antennas are seen at the top of the model positioned over the sternum. The sternum and rib cage are simulated at the upper level of the anatomical model while the spine is simulated at the lower level.

Figure 6B:
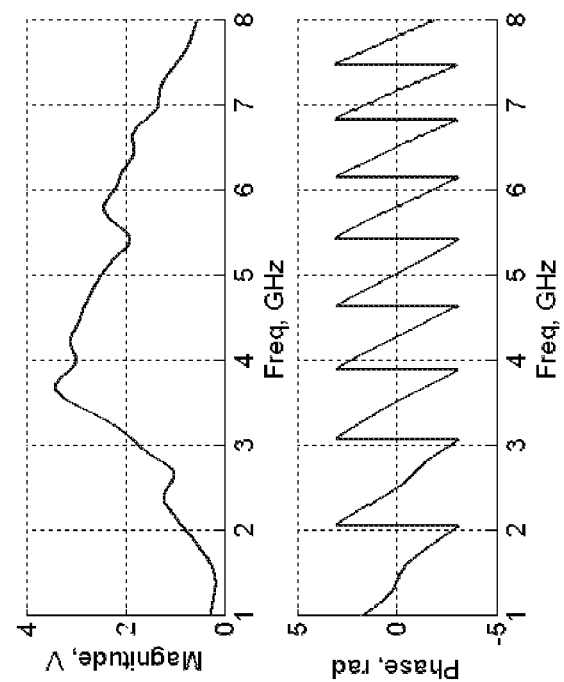
FIG. 6b illustrates the corresponding magnitude and phase of the received reflections in the frequency domain, according to the present invention.
Figure 6A:
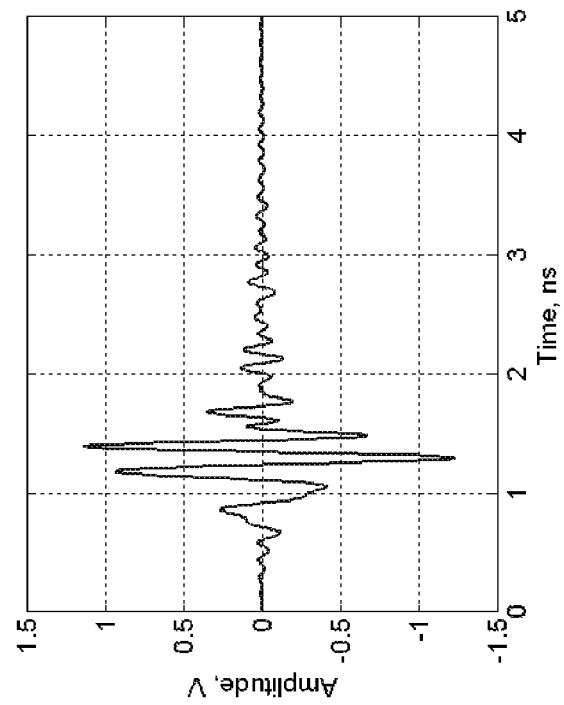
FIG. 6a illustrates the received reflections as viewed in the time domain based upon the FDTD model without a heart of FIG. 5, according to an embodiment of the present invention and using the Bow-tie antenna.

Based on the model of FIG. 5, FIG. 6a illustrates the received reflections as viewed in the time domain while FIG. 6b illustrates the corresponding magnitude and phase of the received reflections in the frequency domain. The received signal has a large initial component resulting from direct coupling between the two antennas. In contrast to the symmetrical spectrum of the transmitted pulse, the energy of the received spectrum is concentrated in the lower frequencies due to increased energy absorption at the higher frequencies.

FIG. 7 illustrates the basic structure of the anatomical model of the present invention with the heart included. Again, the lungs have been omitted for clarity in viewing of the model but were included in the model as tested. The pair of Bowtie antennas are seen at the top of the model positioned over the sternum.

FIG. 8a illustrates the received reflections for the test case with the heart included as viewed in the time domain. FIG. 8b illustrates the corresponding magnitude and phase of the frequency spectrum for the received signal.

Figure 9B:
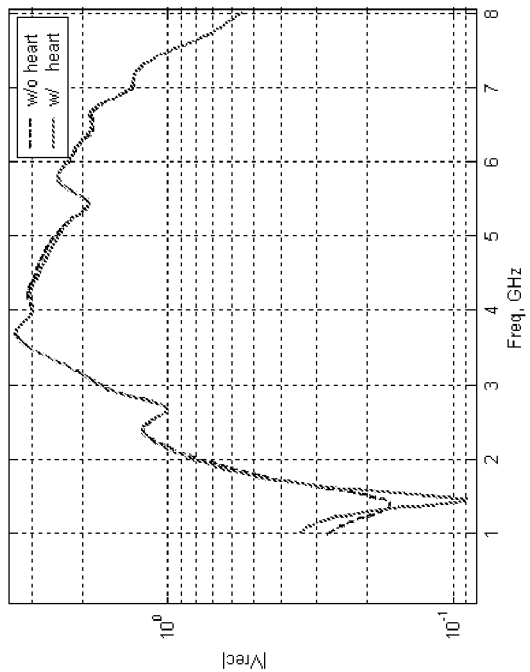
FIG. 9b is a plot of the corresponding spectrum (amplitude and phase) of the time domain difference signal illustrated in FIG. 9a FIG. 10a thru 10h illustrate the received signal for 270 ml thru 200 ml and using the Bow-tie antenna, where 10h illustrates an aggregate of all signals.
Figure 9A:
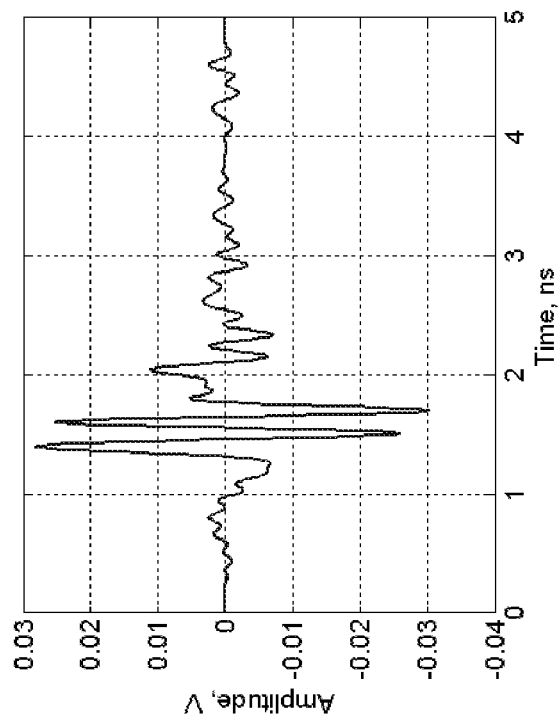
FIG. 9a is a plot of the time domain difference signal calculated by subtracting the data derived from the test case with the heart from the data derived from the test case without the heart and using the Bow-tie antenna.

FIG. 9a provides a plot of the time domain difference signal calculated by subtracting the data derived from the test case with the heart from the data derived from the test case without the heart. The amplitude of the difference signal is 0.058 Vp-p as compared to the 2.35 Vp-p amplitude exhibited by both of the two received signals; a difference of 32.2 dB, establishing an expected minimum sensitivity of the receiver for detection of gross anatomical details based on the simulations. FIG. 9b illustrates the corresponding spectrum of the received signals for the two cases.

With a validated cardiac model, multiple simulations are run against various heart volumes to calibrate the system. For the present invention, a series of eight simulations were run where the total volume of the heart was varied from 200 ml to 270 ml in 10 ml steps. The data corresponding to the maximum heart volume (270 ml) was set as the reference and each subsequent data set was subtracted from the reference set and plotted. With reference to FIG. 10a through 10g, the received difference signals for these seven cases referenced to the maximum volume case are shown.

Figure 10A:
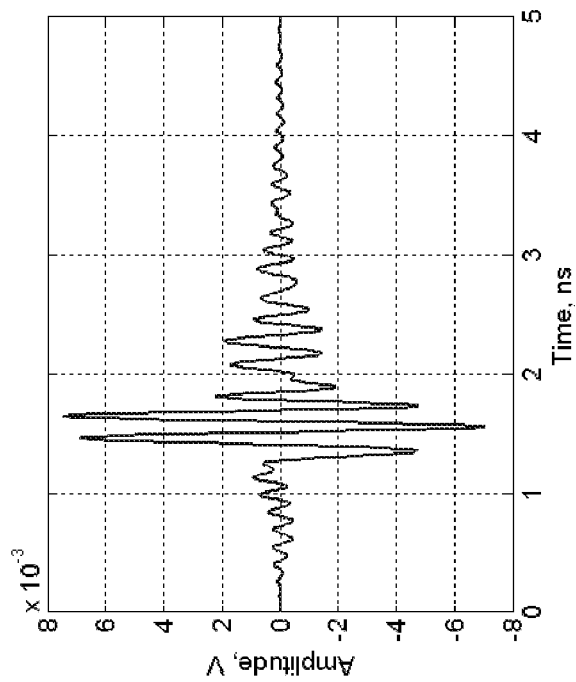
Figure 10B:
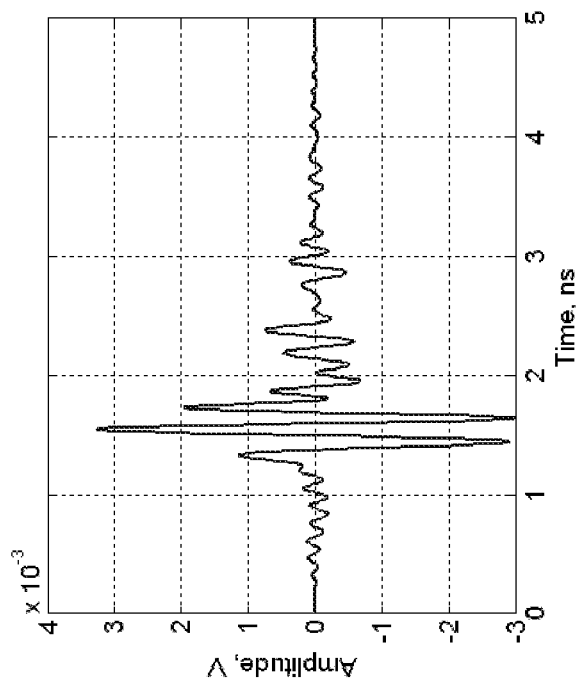
Figure 10C:
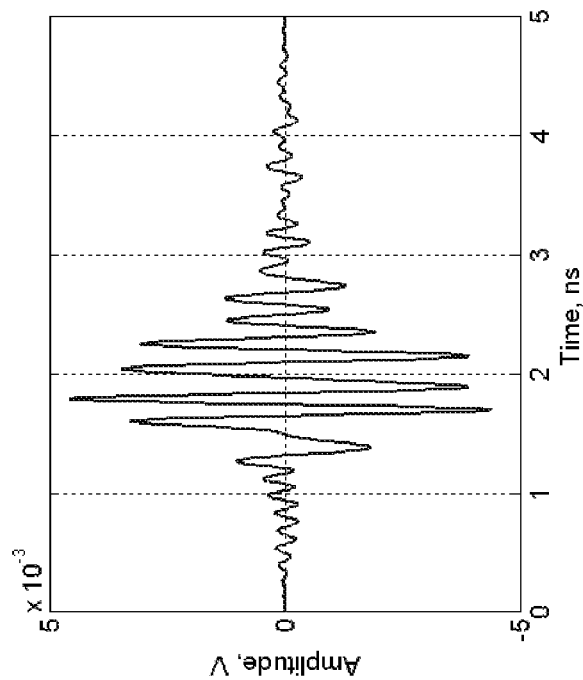
Figure 10D:
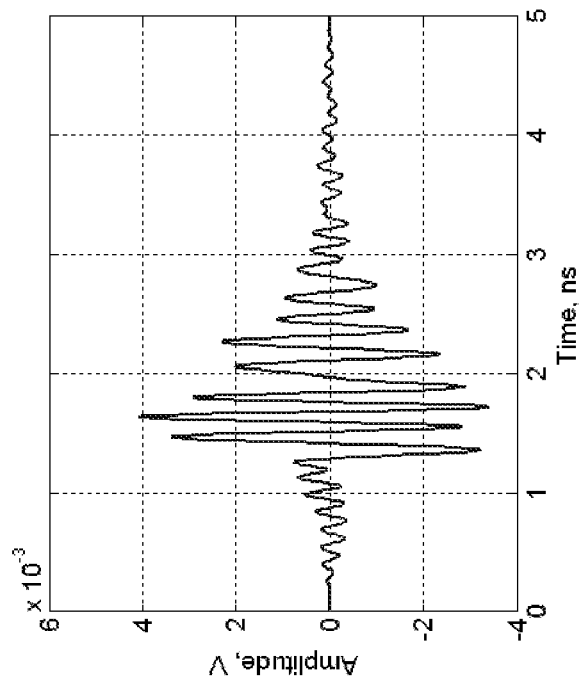
Figure 10E:
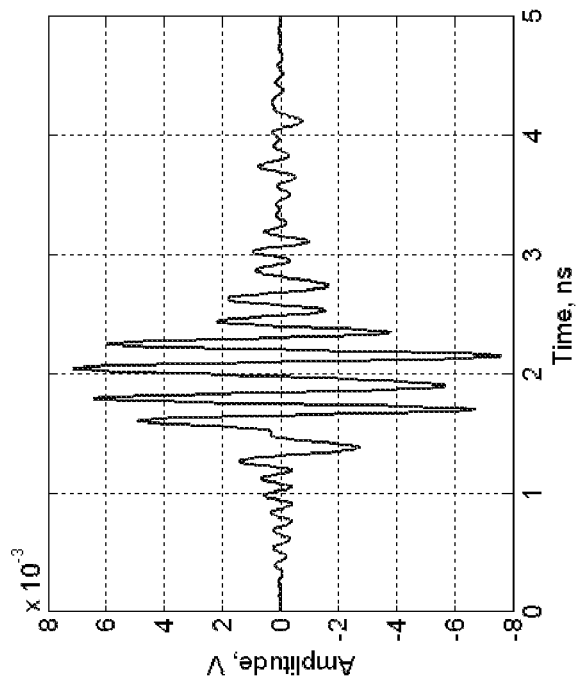
Figure 10F:
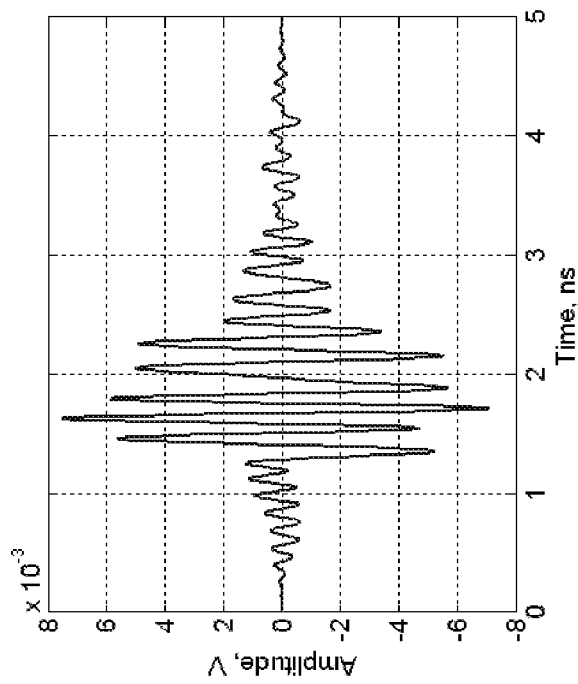
Figure 10H:
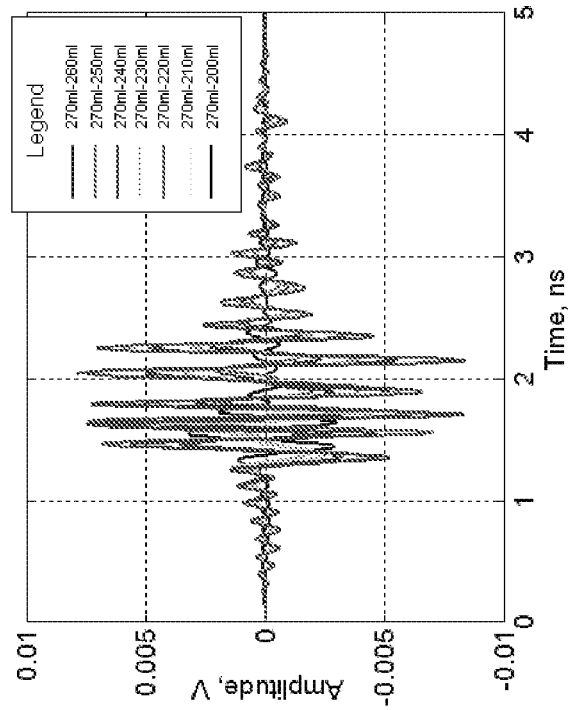
Figure 10G:
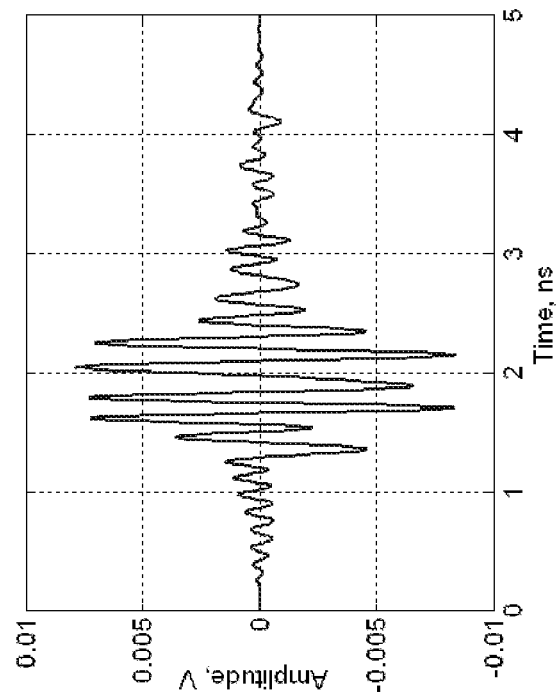

Based upon the simulations, and again with reference to FIG. 10a through 10d, the present invention incorporates an algorithm addressing heretofore-unknown behavior where, as the difference in cardiac chamber volume increases, the length of the difference signal increases. This key relationship is fundamental to the capability of the present invention to determine chamber volume. With reference to FIG. 10h, a plot of all seven difference signals overlaid upon each other is shown. As can be seen, there is an appreciable difference in the difference signals, confirming the ability of the present invention to detect different volumes. The one nanosecond delay between the transmitted pulse and the beginning of the received reflections is due to the finite distance between the antenna plane and the heart wall.

The observable differences of the simulation are presented in a quantifiable form by the computation of the energy of the recorded signal waveform through numerical integration using the following relationship:

$$W = k \cdot \int_0^T s^2(t) \, dt; \qquad [\text{Eq. 2}]$$

where $k$ = normalization factor and $T = 5$ ns, the receiver time window

Figure 11:
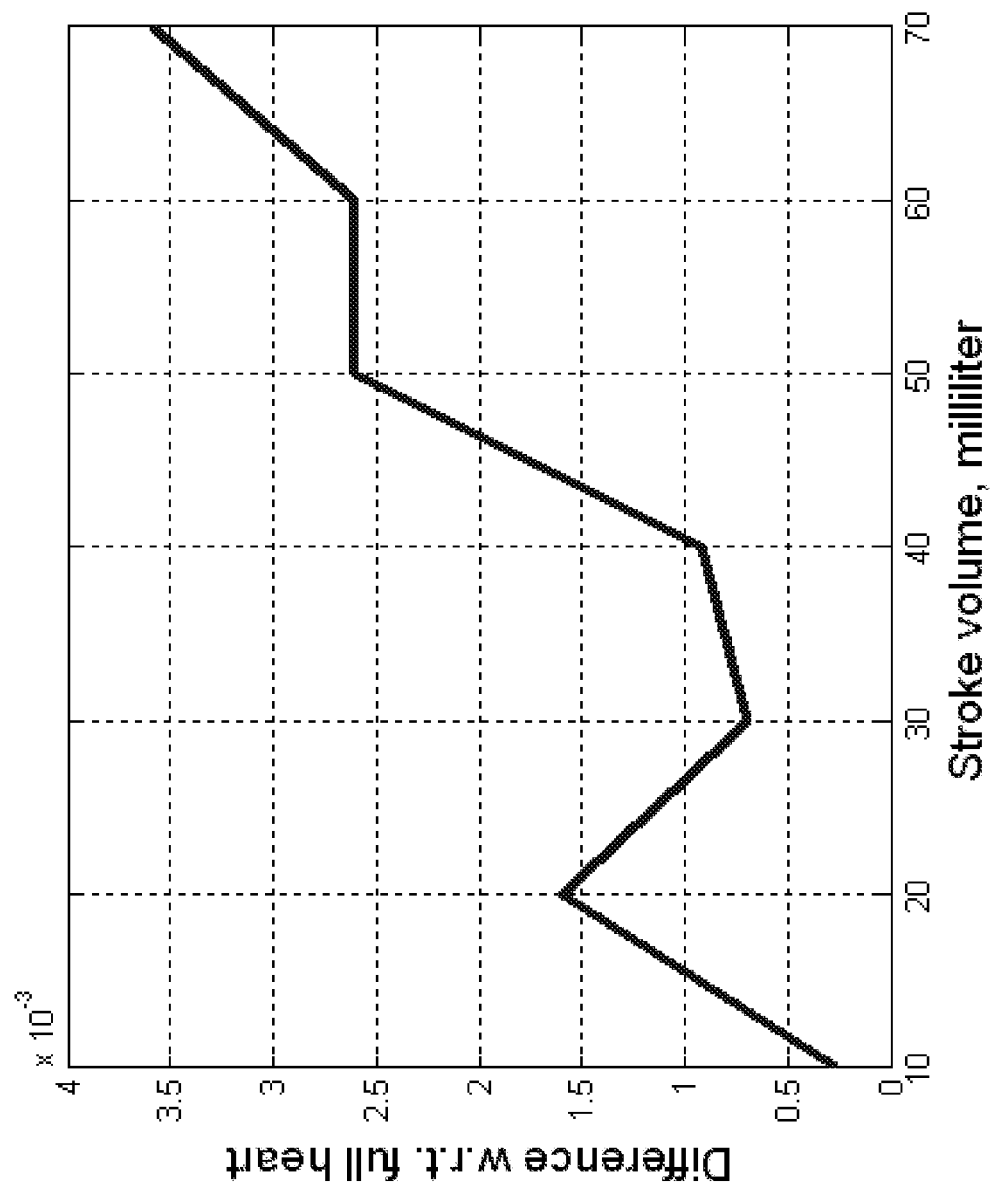
FIG. 11 is a line chart showing the change in received energy with respect to a 270 ml reference volume for stroke volumes from 10 to 70 milliliters using the Bow-tie antenna.
Figure 12A:
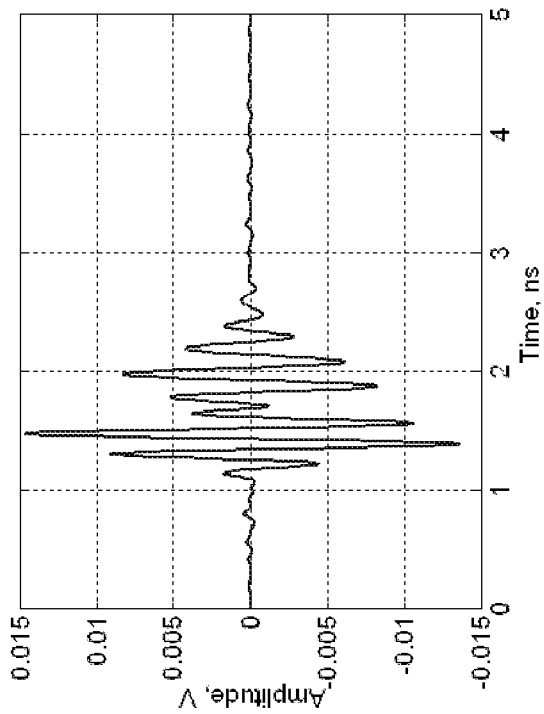
FIG. 12a thru 12h illustrate the received signal for 270 ml thru 200 ml and using the SEE antenna, where 12h illustrates an aggregate of all signals.
Figure 12B:
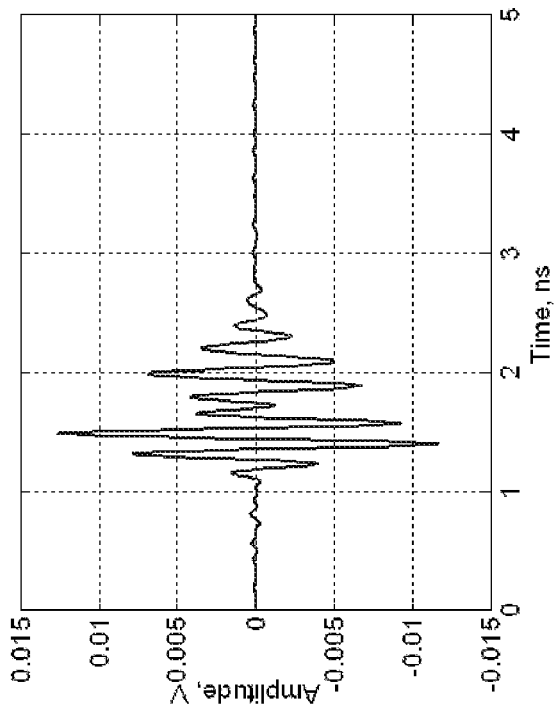
Figure 12C:
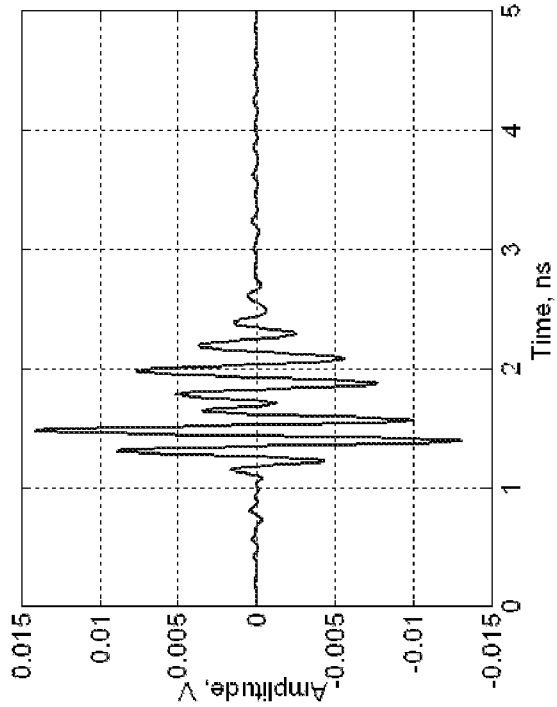
Figure 12D:
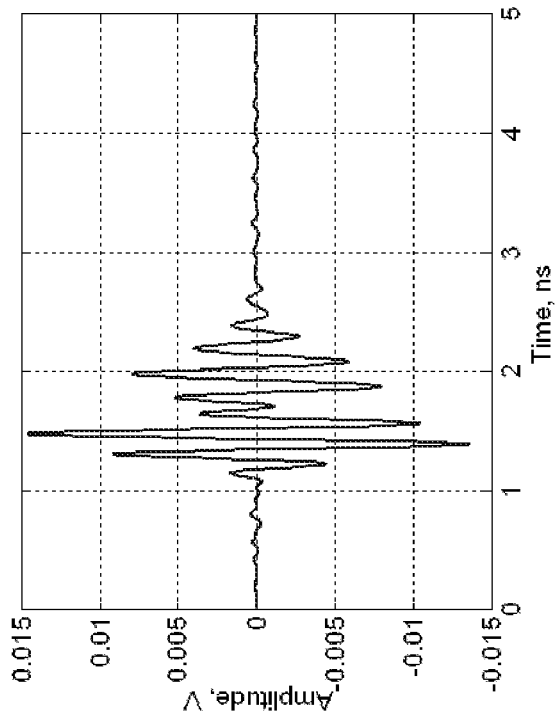
Figure 12E:
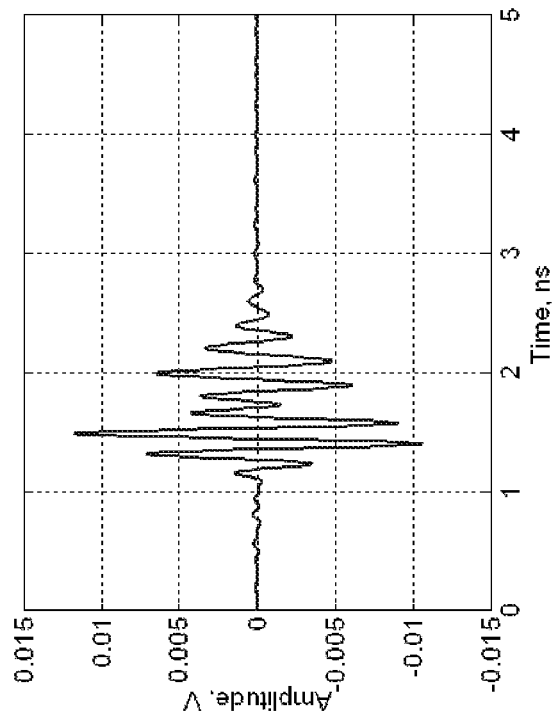
Figure 12F:
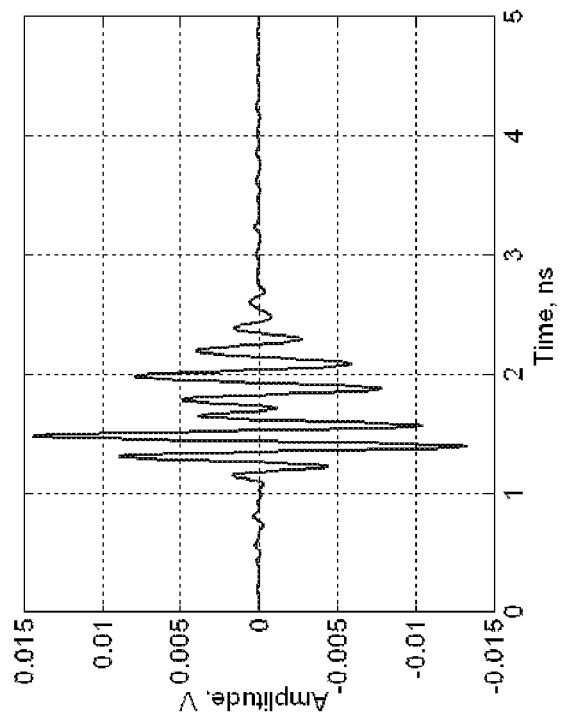
Figure 12H:
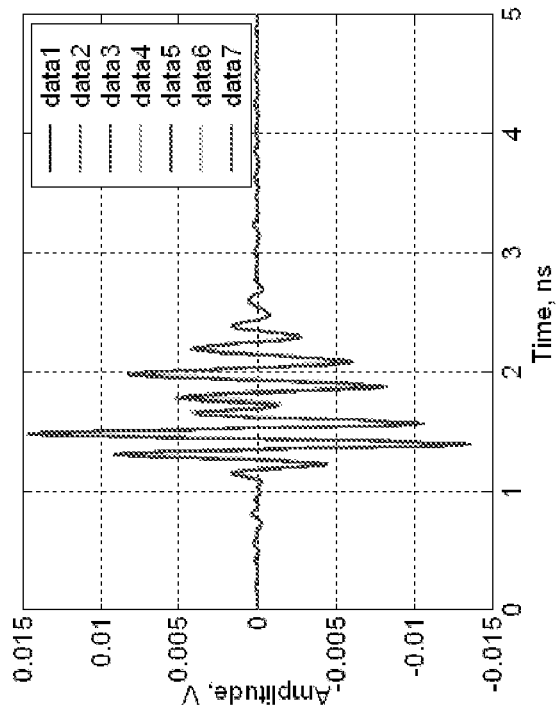
Figure 12G:
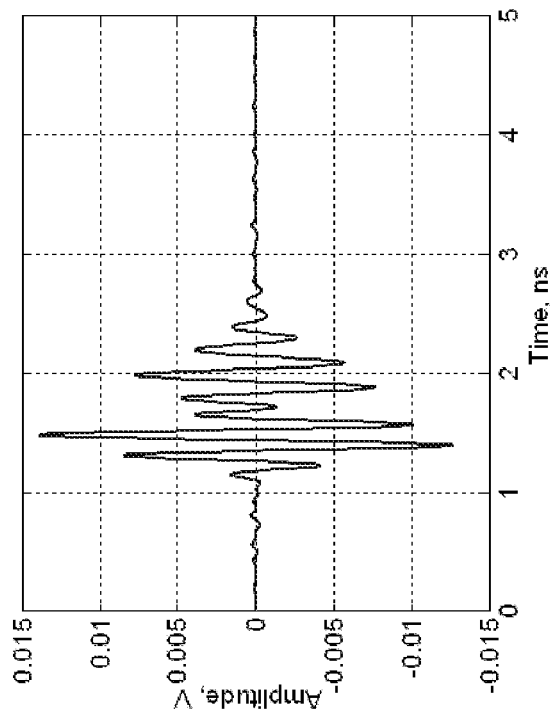
Figure 13:
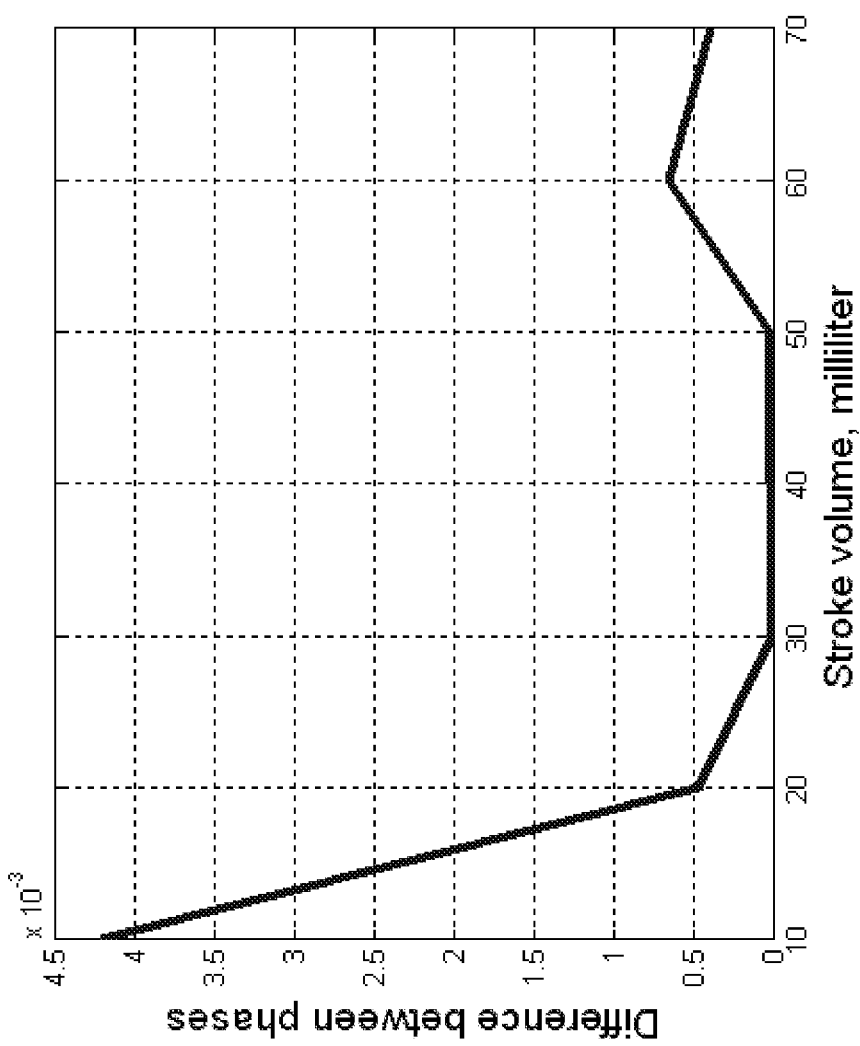
FIG. 13 is a line chart showing the change in received energy with respect to a 270 ml reference volume for stroke volumes from 10 to 70 milliliters using the SEE antenna.
Figure 14B:
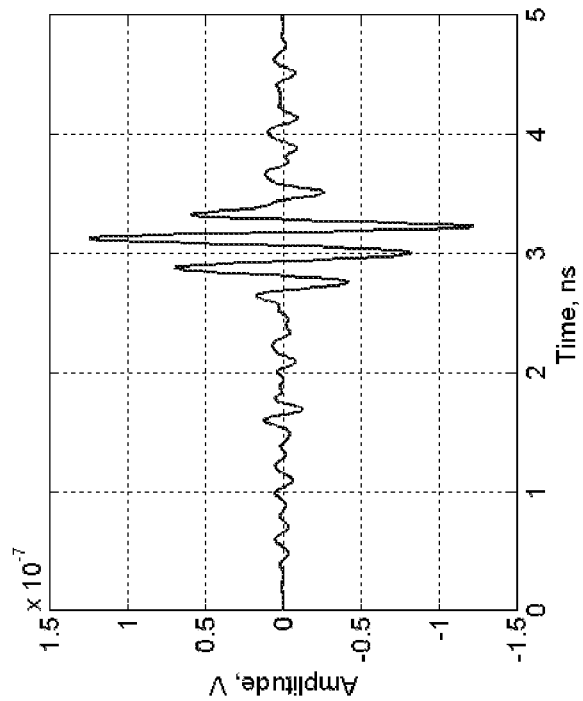
FIG. 14a thru 14h illustrate the received signal for 270 ml thru 200 ml with the SEE antenna placed under the arm, where 14h illustrates an aggregate of all signals.
Figure 14A:
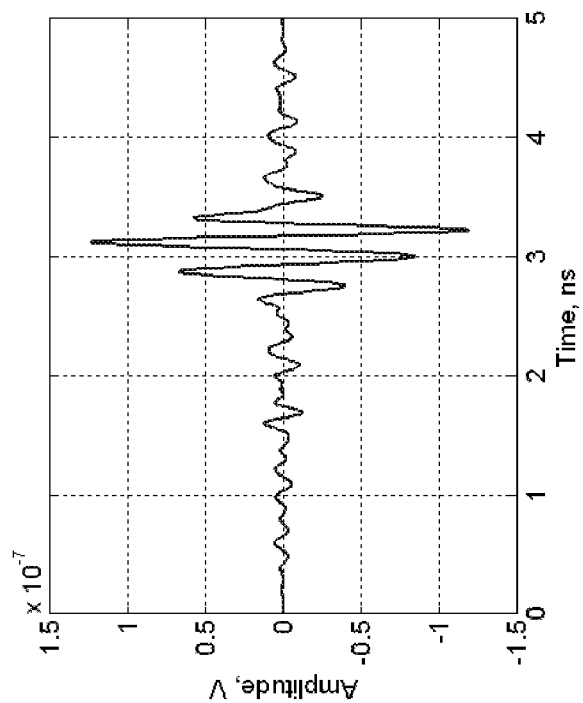
Figure 14C:
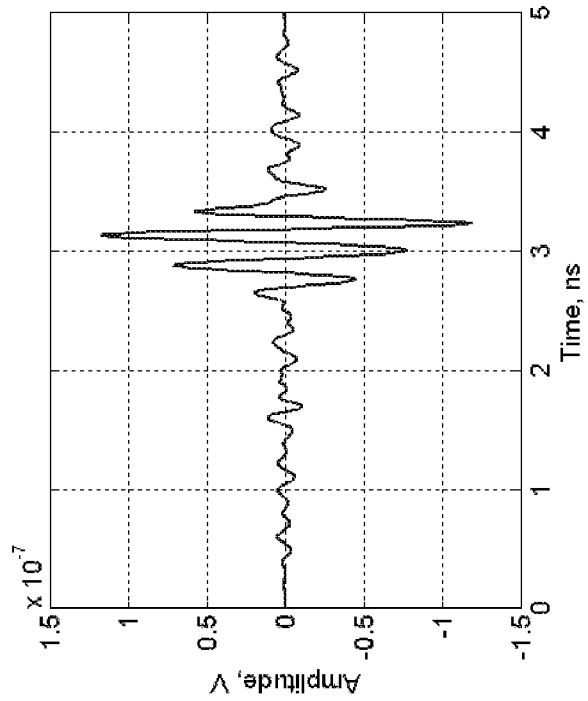
Figure 14D:
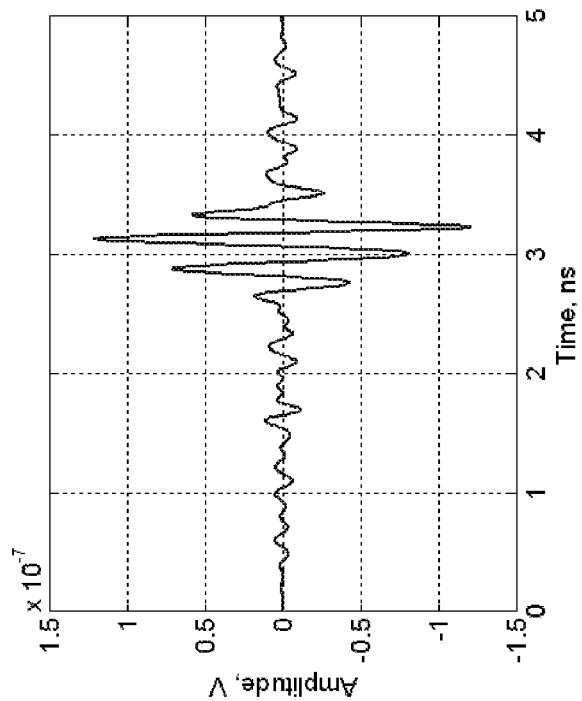
Figure 14F:
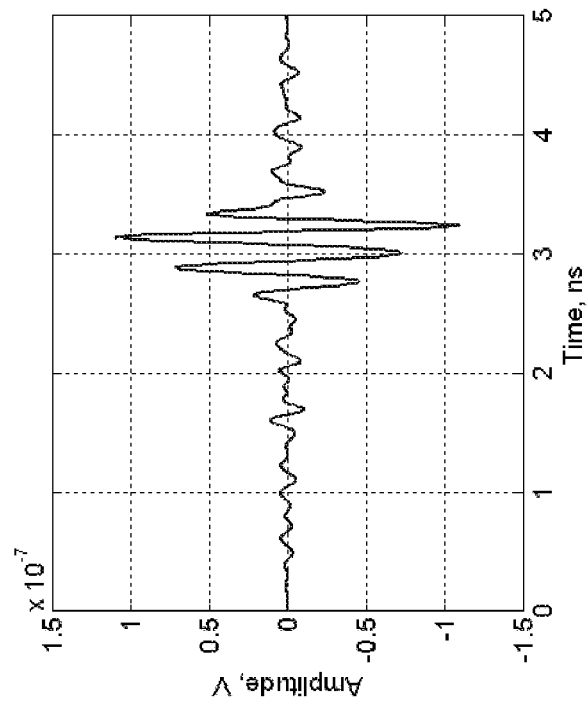
Figure 14E:
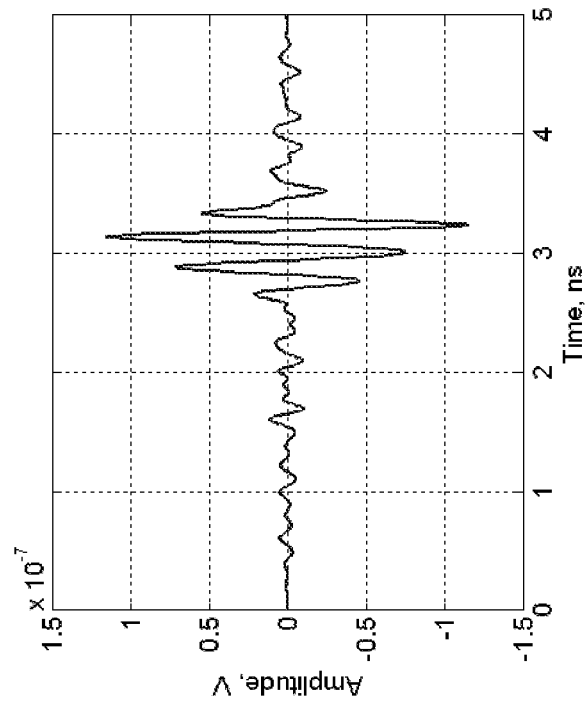
Figure 14H:
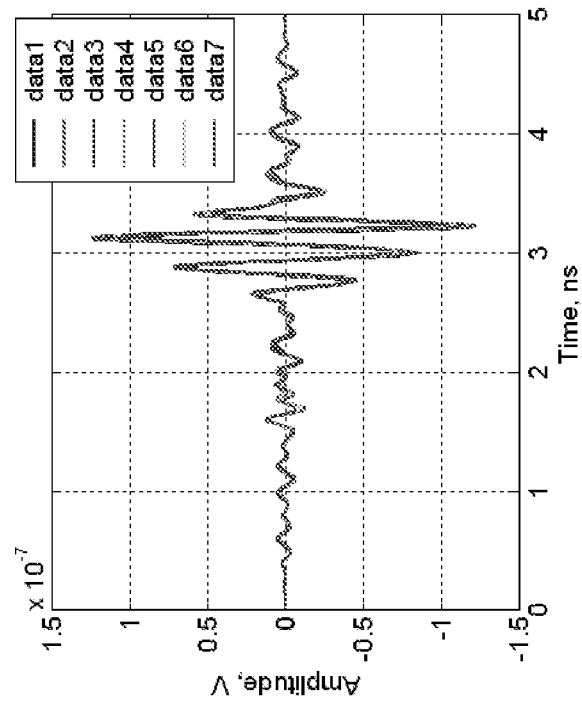
Figure 14G:
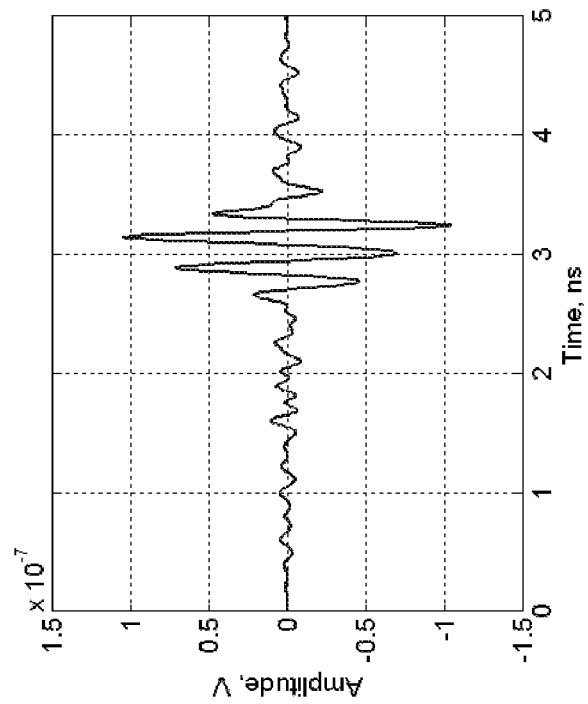
Figure 15:
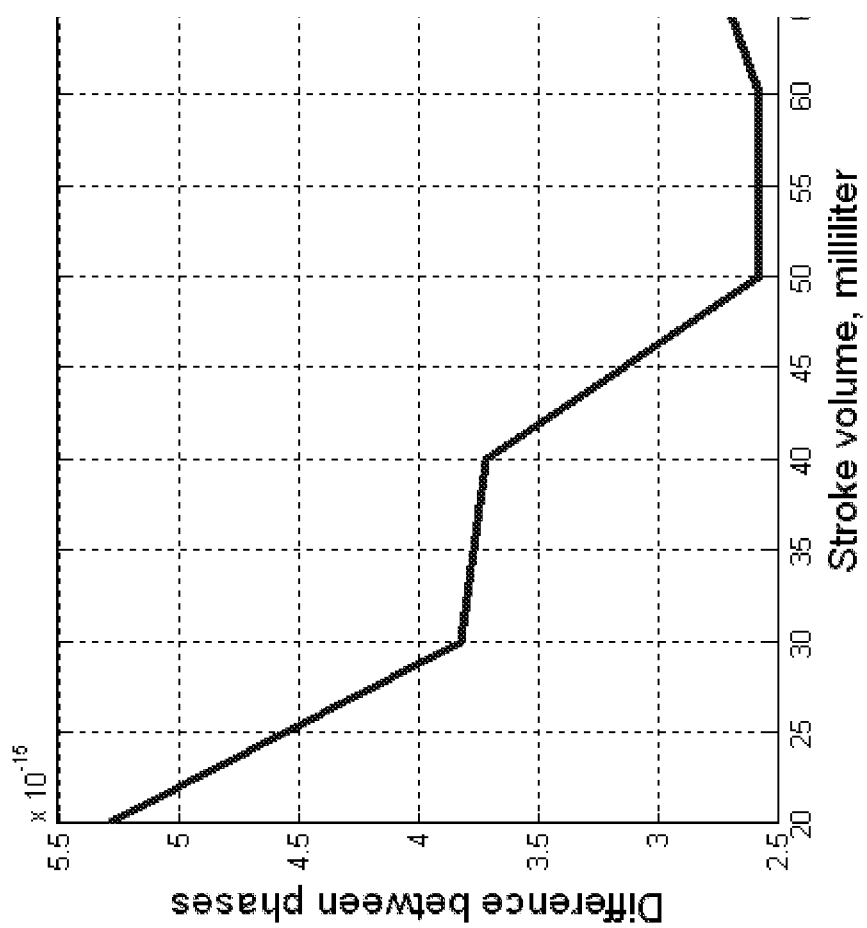
FIG. 15 is a line chart showing the change in received energy with respect to a 270 ml reference volume for stroke volumes from 10 to 70 milliliters using the SEE antenna placed under the arm.

FIG. 11 provides a graphical representation of the energy contained in the difference signals. The horizontal axis represents the difference in volume with respect to the maximum volume case (270 ml) while the vertical axis represents the difference in energy. As can be readily observed, the graph is not monotonic but does include two data values (30 ml and 40 ml) respectively where the energy in the difference signal resulted in a slope reversal.

As illustrated in FIG. 11, increases in reflected energy correlate with larger differences in chamber volumes, indicating the ability to measure variations in the volume of the human heart with the UWBMR.

The present invention incorporates novel geometrical models and functional algorithms, which account for various nonlinearities and provide an excellent correlation between heart surface area and volume. In a further embodiment of the present invention, the UWBMR also provides an initial three-dimensional empirical measure of the size and shape of each heart, which is then used by the CPU and associated software to generate a significantly more accurate measure of the actual volumetric changes of a specific individual's heart.

The present invention provides accurate assessment of changes in cardiac chamber volume and stroke volume to provide useful diagnostic information, irrespective of the size and shape of a subject's heart. In a further embodiment of the present invention, the software allows the specific heart shape and size to be changed to account for expected differences as a result of age, muscularity, or other factors to produce more accurate absolute assessments of stroke volume and changes in stroke volume.

In a still further embodiment of the present invention, the software of the UWBMR system is able to ingest data from other imaging systems such as MRI or CT, for use in determining the shape and size of a particular individual's heart to increase the accuracy of stroke volume measurements. In this circumstance, the 3-D information obtained from other imaging systems is adapted to the specialized model correlated to the UWBMR.

In a still further embodiment of the present invention, the UWBMR includes a targeting element that allows the primary signal to be directed to a key focal point on the heart's surface to maintain consistent and accurate measurements. This additional feature considers adjustments to each model required to accommodate changes in the position and orientation of the heart during the cardiac cycle with respect to the placement of the radar antenna. In the initial model, our simulations assumed the antenna was focused on the heart center of mass in the same position for different phases of the cardiac cycle. In this further embodiment of the present invention, the UWBMR system automatically and continually adjusts the direction of the transmitted signal to maintain a consistent view of the focal area of the heart, and, make appropriate adjustments to the perceived volumetric changes by integrating the dynamic behavior of the heart during the cardiac cycle.

In an additional configuration, the present invention uses and includes data from a similar series of simulations using the SEE antennas. After plotting the difference in the received signals as shown in FIG. 12a-12h and FIG. 13, there was a significant difference in the observed behavior between the bow-tie and SEE antennas. In the simulations, the elliptical antenna used in animal trials did not perform as well as a simple bow-tie antenna. This difference is partially due to the fact that the bow-tie antenna is physically larger and has improved directivity when compared to the elliptical antenna. Consequently, in a best mode, the present invention would employ a bow-tie antenna configuration. In addition, a second basis for performance differences between the bow-tie and SEE antennas is differing start frequencies. The bow-tie antenna used a start frequency of 1 GHz, while the SEE antenna used a start frequency of 3 GHz. The absorption of RF energy by the body at the lower frequencies (1 GHZ) used by the bow-tie antennas is significantly lower, resulting in stronger received reflections. Consequently, in a preferred embodiment of the present invention, the antenna is a bow-tie antenna using a starting frequency of 1 GHz. However, to comply with existing regulatory requirements, another preferred embodiment uses a starting frequency of 3 GHz.

According to the method of the present invention, guidelines for antenna placement optimize the operation of the UWBMR. Antenna placement can be a critical parameter affecting the strength of the received reflections used to calculate cardiac chamber volume. In a preferred embodiment, and a best mode of operation, the antenna is placed on a subject's chest at the sternum. In particular, the antenna is placed within a 2.5 cm radius from the center of the sternum.

The antenna may be placed at other locations to capture cardiac motion, such as under the left arm, but measurement and calibration will differ. FIG. 14a through 14h and FIG. 15 provide a comparison of results from application of the UWBMR with differing antenna placements. Consequently, in a preferred embodiment of the present invention, the antenna is placed in close proximity to the subject's sternum rather than on the side chest wall, under the arm. Placement on the sternum provides a consistent calibration approach to maximize the resolution and accuracy of the cardiac imaging process. With an equivalent signal spectrum and energy, placement of the UWBMR antenna under the arm can cause additional attenuation of transmitted and reflected signals due to the increased distance of the antenna from the heart.

The present invention, incorporating a single UWBMR provides a reliable yet flexible foundation for monitoring cardiac stroke volume and for conducting laboratory experiments for improving the resolution of measurements of changes in stroke volume. In a further embodiment, two UWBMR transceiver units are integrated to create a two-element radar array. The two units are operated simultaneously but incoherently to allow collection of two independent data streams simultaneously, thereby enhancing the overall image resolution and volumetric accuracy.

As earlier indicated, the position of the radar antenna affects the quality and strength of the received cardiac signals. In a best mode, present optimal position for the radar antenna is on a subject's chest directly over the center of the sternum within a placement window of approximately 5 cm diameter. Consequently, in a preferred embodiment, the antenna is preferably located within the 5 cm circle over the center of the sternum. Additionally, in a further configuration a multi-antenna array may be employed where the size of each antenna is smaller to allow at least two antennas to be arrayed over the sternum. Further resolution may be achieved by balancing the antenna sizes and placement. Consequently, additional embodiments include multi-sensor arrays deployed in close proximity to the targeted area, in this case, the heart. To simplify testing, the UWBMR system having a single optimized UWBMR transceiver was used in conjunction with enhanced algorithms.

Figure 16:
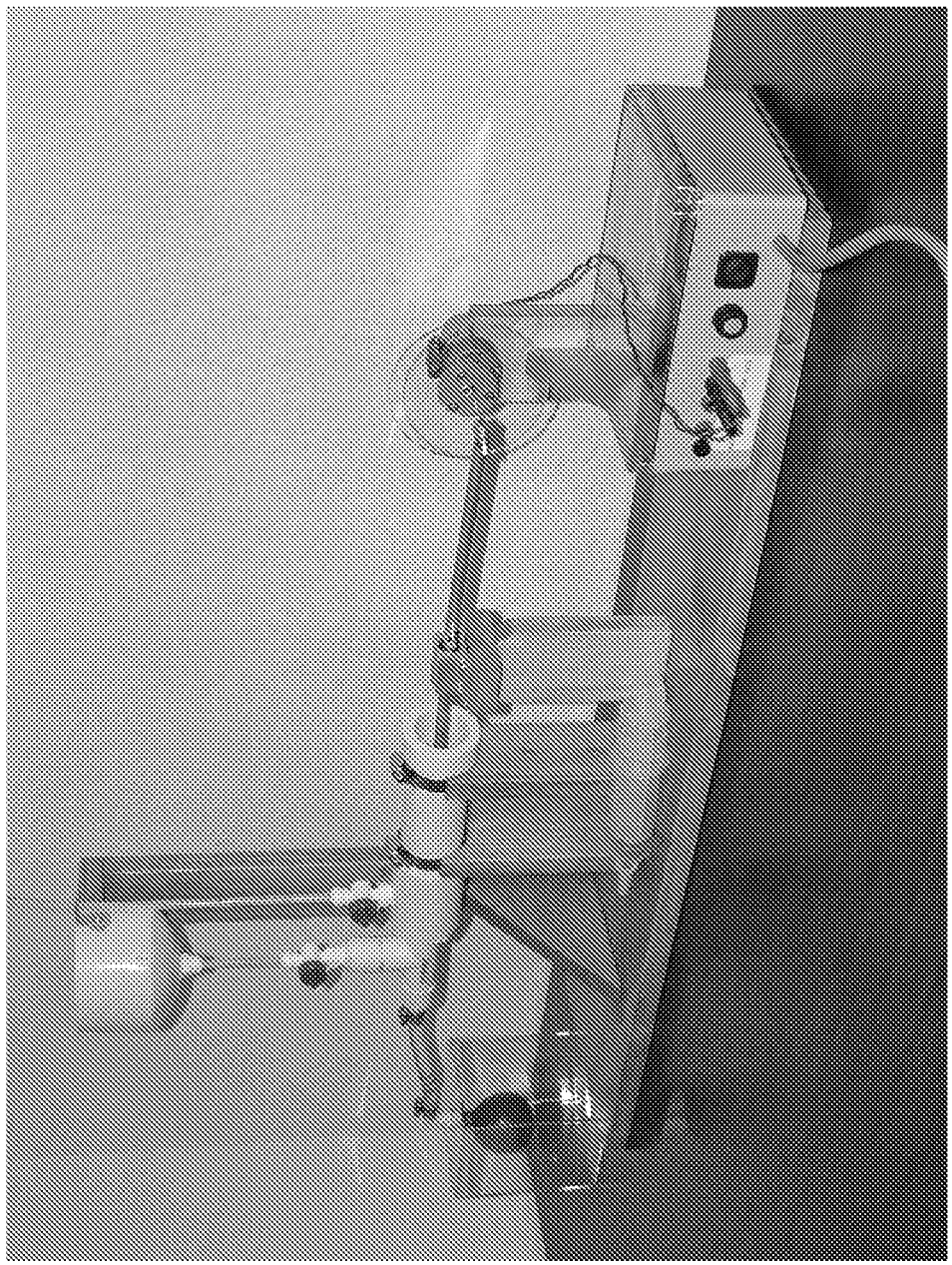
FIG. 16 is an image of the single chamber cardiac phantom used in collecting empirical data.

Prior UWBMR development efforts have relied on testing hardware and algorithms against a simple mechanical phantom. The simple mechanical phantom uses a stepper motor to move a small metal target back and forth along the bore sight of the radar antenna, thereby simulating motion. The challenges inherent in developing a system to measure cardiac chamber volume required a more sophisticated phantom capable of mimicking the mechanical and cyclical function of the heart, with the inclusion of heterogeneous tissues having different dielectric constants. As shown in FIG. 16, the present invention incorporates algorithmic elements derived from the use of a Single Chamber Cardiac (SCC) phantom.

The SCC phantom is designed to simulate an adult left ventricle chamber. The SCC includes a power supply, a geared DC motor, a drive linkage, a piston assembly, and an elastic chamber. The power supply provides the motor with the necessary voltage and current required to drive the motor. The geared motor rotates at a constant speed and is connected to the piston by a drive linkage. As the motor spins, the rotational motion of the drive wheel is translated into linear motion by the drive linkage, causing the piston to move back and forth within the cylinder. The piston's back and forth motion forces liquid into and out of the elastic chamber, inflating and deflating the chamber, and simulating the physiological function of a heart's ventricle chamber during a cardiac cycle. The piston/chamber geometry was designed to provide a change in volume during a cycle of approximately 75 ml, equivalent to the typical stroke volume of a healthy adult male. In the present invention, the piston diameter is 4.0 cm, while the stroke of the piston is 6.0 cm, yielding a displacement of 75.4 ml. Other piston diameters and strokes may be used to perform simulations having other parameters.

In practice, the chamber and cylinder are pre-filled with liquid and all air is removed through the valve and reservoir assembly prior to operation. The minimum chamber volume corresponding to cardiac systole is initially set by placing the piston in the maximum displacement position and filling the elastic chamber to the desired volume using a 10 cc syringe. Once filled, the drive motor is started and the radar enabled.

During simulation, the UWBMR transmits a series of pulses toward the elastic chamber as it inflates and deflates. Some of this energy is reflected back to the UWBMR due to the large difference in dielectric properties between the air, the surface of the elastic chamber and the liquid in the phantom. In a first embodiment of the SCC phantom simulation, the UWBMR antennas are located approximately 20 cm away from the center of the chamber to provide a comparable time of flight of the radar signals in the body based on an average relative dielectric constant in the body of 50 and a 3 cm distance from the chest surface at the sternum to the LV wall of the heart. This relationship is described in Equation 3, below. The radar output of the UWBMR is connected to stereo audio inputs located on the soundcard in the PC. While the phantom is active, the reflections are captured and stored on the hard drive of the PC for post-capture analysis.

$$T_{flight} = \frac{2D\sqrt{\varepsilon_r}}{c};$$ [Eq. 3]

where $D$ = distance from radar to object, $\varepsilon_r$ = dielctric constant of media, and $c$ = speed of light in *freespace* $(3 \times 10^{10}$ cm/sec$)$ The present invention incorporates an advanced algorithm used in conjunction with the signal-processing module to support capture and processing of desired data to determine stroke volume.

A one-dimensional study of a measurement algorithm allowed calculation of the rate and linear displacement of a moving target. An original mechanical phantom having a metal target was used to simulate wall motion. The metal target in air was reciprocated over a 10 cm range at rates ranging from 20 to 80 BPM. A 10 cm displacement in air is roughly equivalent to a 1.5 cm displacement in the body due to the reduction in propagation speed resulting from the dielectric properties of human tissue as discussed previously. Separately measured displacement of the target matched the calculated results produced via the UWBMR with the algorithm operating on the radar returns while the rate of the displacement was within the accuracy of the FFT and the measurement equipment.

Figure 17:
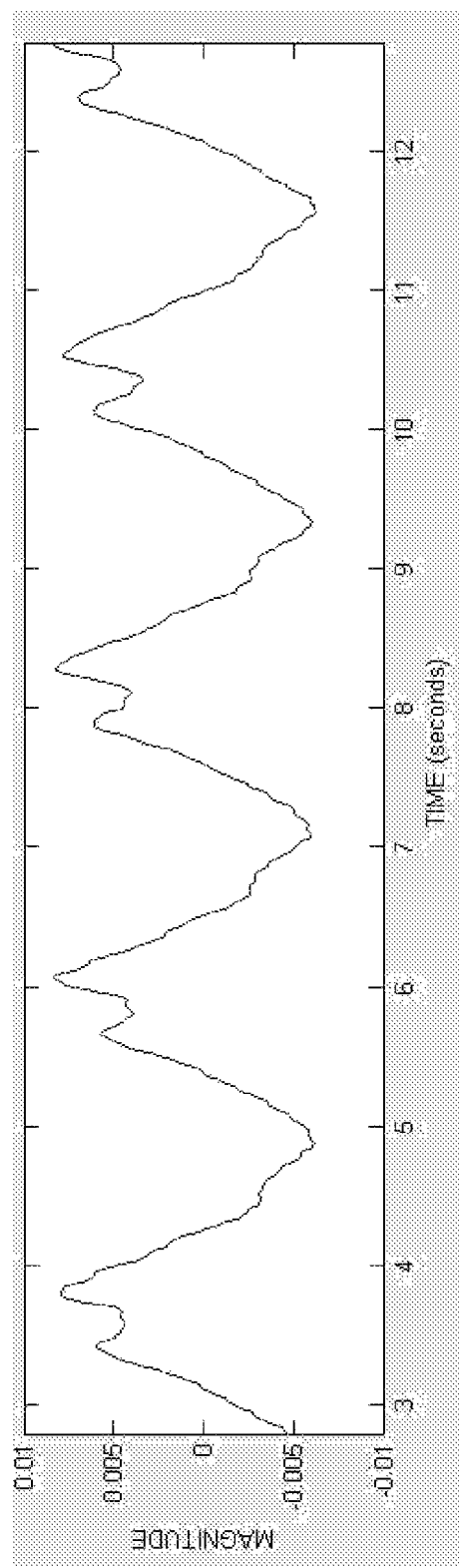
FIG. 17 is a line chart of a typical received signal collected from the SCC phantom over time.

Once calibration of linear motion had been completed, the three-dimensional single chamber cardiac phantom was employed to further calibrate the UWBMR and to support modification of the software and algorithms of the invention. The single chamber cardiac phantom was operated and empirical radar data was collected. This data was used to further refine chamber volume algorithm and associated software. During simulation, with the phantom actively operated through simulated cardiac cycles, the UWBMR proceeds to quantize the received radar signal in the time domain to yield a series of range bins. Each range bin contains the received signal for a small increment in time and the data in that bin corresponds to the reflections emanating from a range or depth equivalent to the time of flight of the radar signal for that depth. With reference to FIG. 17, a typical time domain waveform collected from a single radar bin using the single chamber cardiac phantom is shown.

Figure 18:
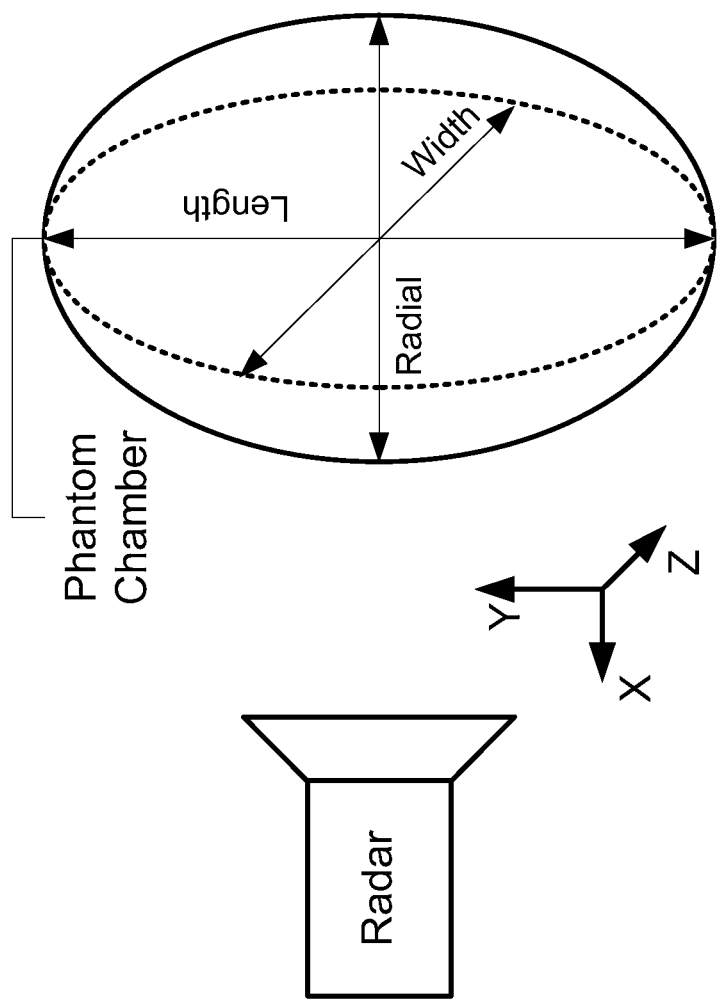
FIG. 18 is an illustration of the geometry of the phantom chamber model used to collect empirical data.

The UWBMR represents a novel medical imaging component where analog approaches are combined with the UWBMR in estimating cardiac chamber volume. With reference to FIG. 18, an ellipsoid model was used for the expandable chamber of the phantom. The major axis, designated as the "Length" runs parallel to the Y-axis. The two minor axes are designated "Radial" and "Width" with the radial axis parallel to both the X-axis and the bore sight of the radar antenna.

According to the method of the present invention, the UWBMR was used to collect and process signal reflection data from the phantom for the three pre-fill cases. Three test cases were created with pre-fill values of 12 ml, 43 ml, and 64 ml where the pre-fill amount corresponds to the cardiac systole state. The chamber axes were measured with a set of calipers at systole and diastole for all three test cases, allowing calculation of the systolic and diastolic volume and the stroke volume.

Figure 19A:
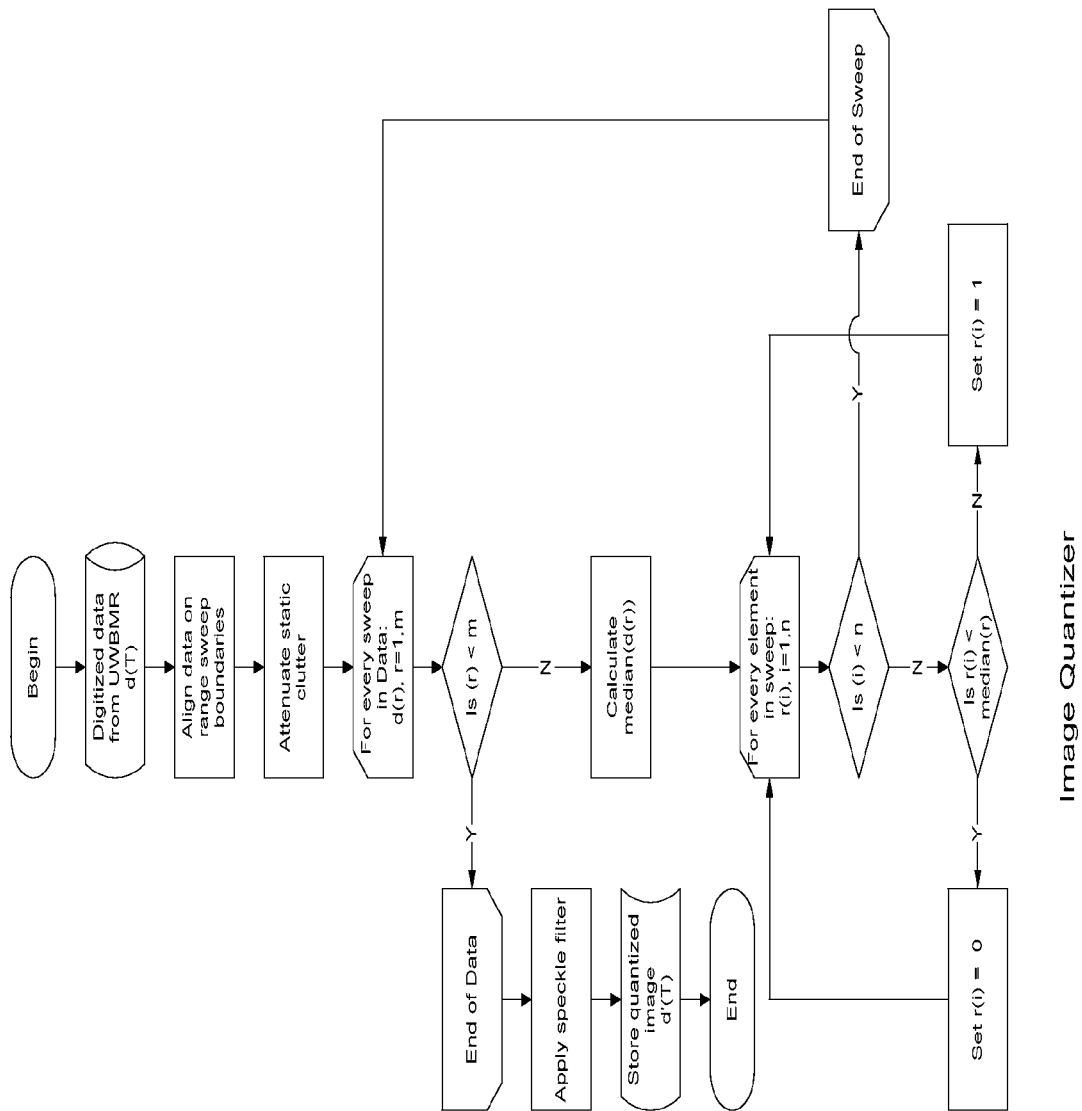
FIGS. 19a and 19b are block diagrams of the machine vision algorithm according to the present invention.
Figure 19B:
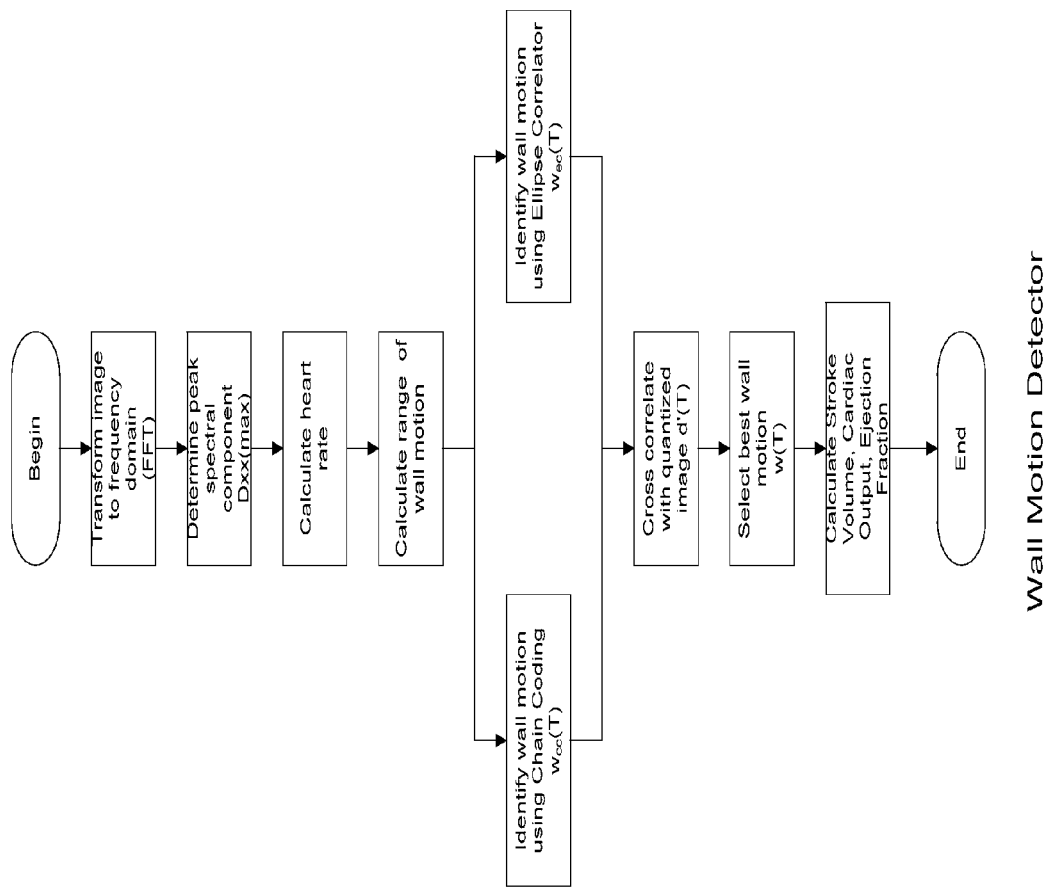
Figure 20:
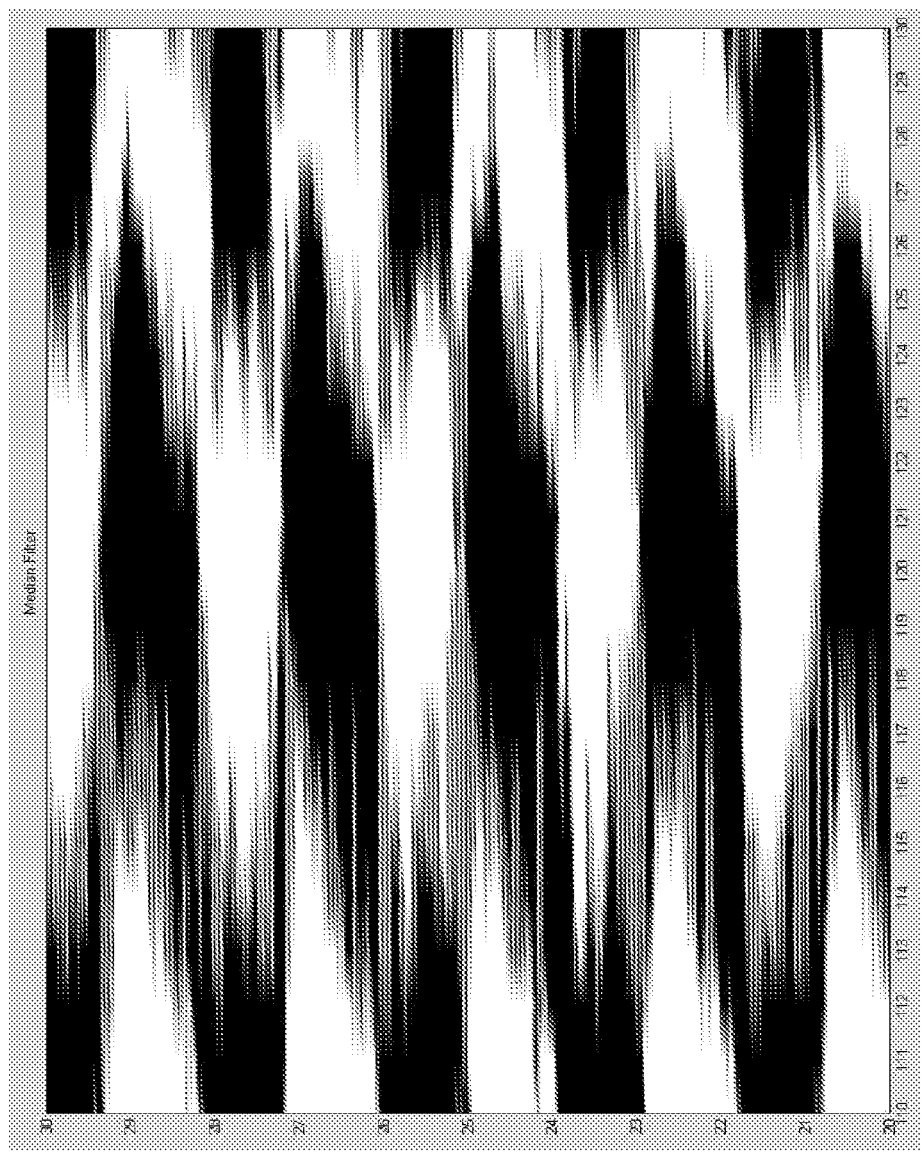
FIG. 20 is an image of the spatial domain view of the phantom chamber versus time, according to the present invention.

A block diagram of the processing is shown in FIGS. 19*a* and 19*b*. The raw radar data is first aligned on scan boundaries and passed through a series of high pass filters to remove static clutter (reflections from inanimate objects) and lower frequency noise. The resultant motion data is then amplified and quantized to produce an interim black/white image. Next, a speckle filter with a 3×3 kernel is applied to remove random speckle noise. FIG. 20 shows a typical spatial plot of the processed received signal for bins 110 to 130 over a period of 10 seconds. The white sinusoidal pattern (primary axis for the sinusoid is vertical and centered on bin 124) represents the motion of the phantom surface closest to the radar antenna. This plot contains approximately 4.5 cardiac cycles.

In the next stage, the median value of the bounded white section is calculated for every row in the image space. Additionally, the minimum and maximum number of bins is calculated for every cardiac cycle. The difference in the maximum and minimum bin numbers is multiplied by the spatial resolution of the test system. In the initial simulations, the spatial resolution was 0.193 cm/bin based on 110 cm total range and 570 bins. With this information, the UWBMR is able to measure the change in the radial axes of the chamber between systole and diastole. In a first embodiment, the method of the invention presumes that the radial and width axes of the chamber are basically equal and have the same rate of change. Additionally, the method of the invention presumes that the length axis does not change at the same rate as the other two axes. Using a best-fit approximation, the UWBMR determined that the length axis changes at an exponential rate of 0.635 with respect to the minor axes. For each of the three test cases, we arrived at the diastolic volumes and stroke volumes using the measured values for the systolic chamber volume and the change in volume as calculated from the radar data.

Empirical data gathered via use of the single cardiac chamber phantom in conjunction with earlier theoretical simulations were used to further develop the advanced algorithmic approaches deployed in software in the present invention to support measurement of stroke volume. The UWBMR, based on the refined algorithm relationships, was able to detect and measure relative changes in the volume of the balloon. The use of the SCC phantom allowed development of the basic algorithm associated with the method of the invention without having to initially employ animal models.

Figure 21:
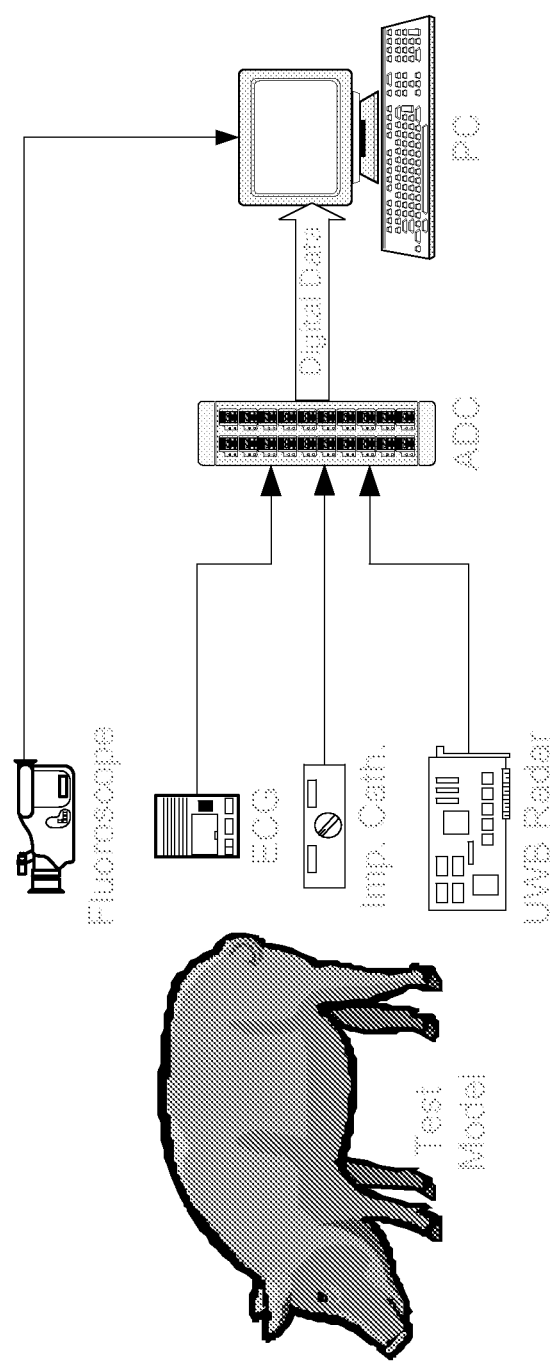
FIG. 21 is an illustration of the data acquisition system used for collecting empirical data in conjunction with data from other sensor systems, according to the present invention.

The modified UWBMR was then used in testing on porcine animal models to further refine and validate the system. The data acquisition system included the UWB radar, a 3-lead ECG, an impedance catheter, a multi-input analog-to-digital converter (ADC), a fluoroscope, and a personal computer as shown in FIG. 21. The analog outputs from the ECG (lead II) and Impedance catheter were connected to channels one and two respectively of the ADC. The synch output of the UWB radar was connected to channel three of the ADC while the video output of the radar was connected to channel four. The digital output of the ADC was connected to the personal computer. The video output of the fluoroscope was connected directly to the video input port on the PC.

Figure 22:
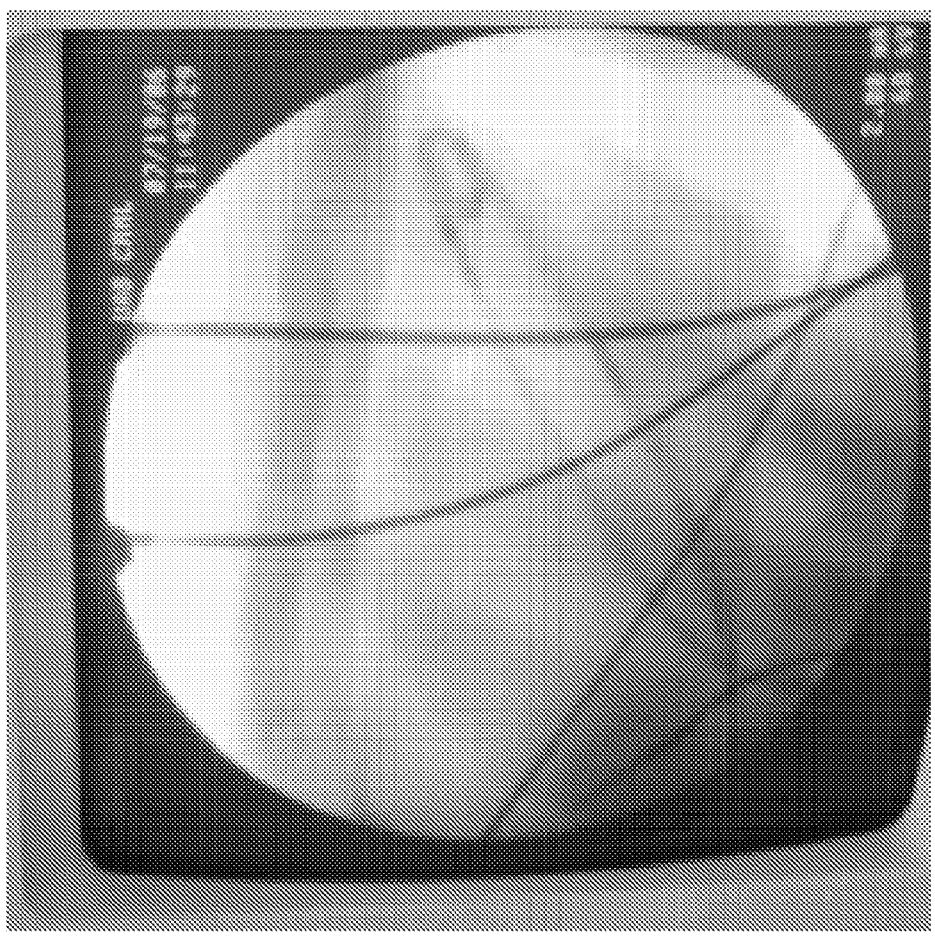
FIG. 22 is a fluoroscopic image of the catheter deployed in the porcine model for use in calibration and confirmation of sensory results from the UWBMR sensor, according to the present invention.
Figure 23:
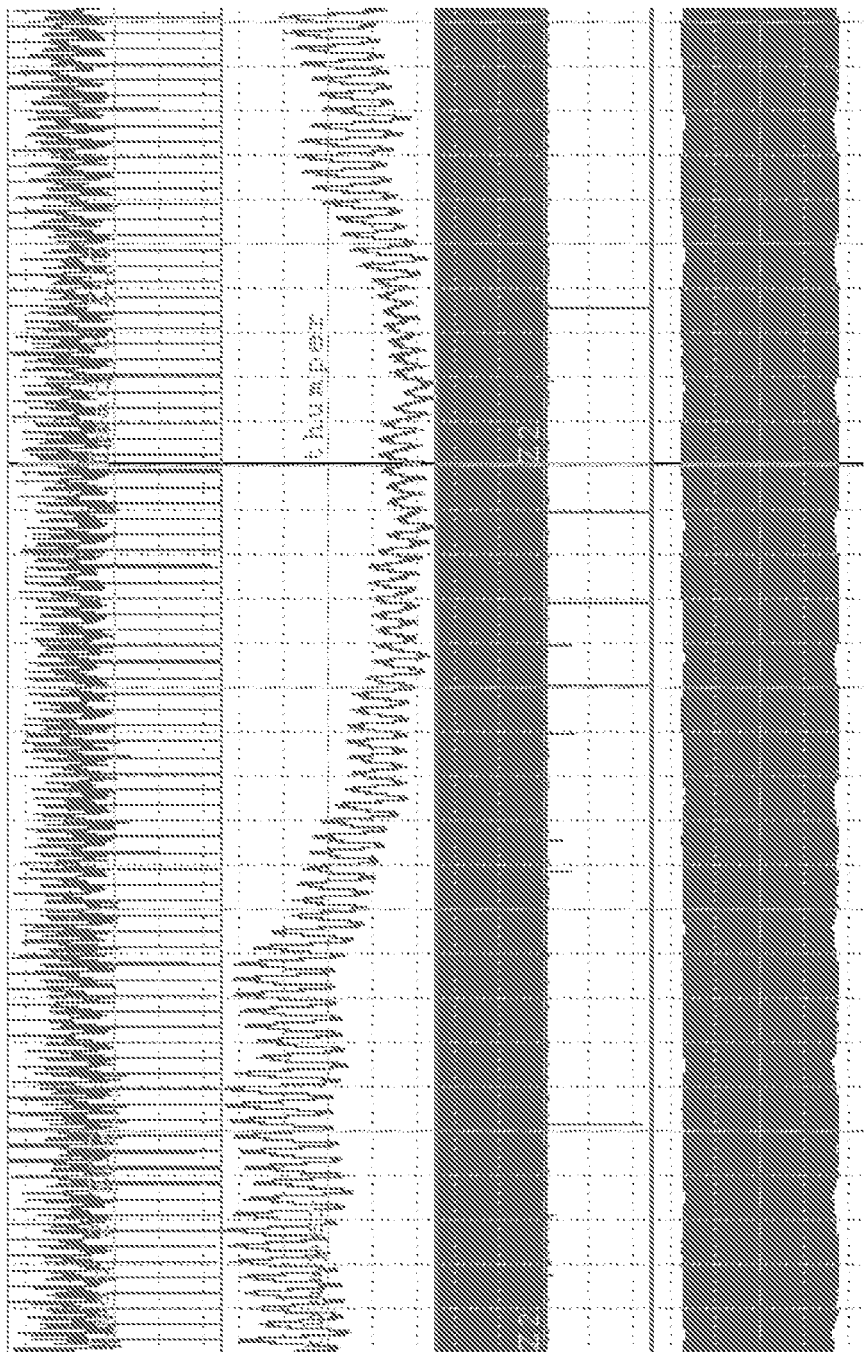
FIG. 23 is an illustrative comparison of the signals received over time from the UWBMR sensor and other sensors, including, ECG and impedance, according to the present invention.
Figure 24:
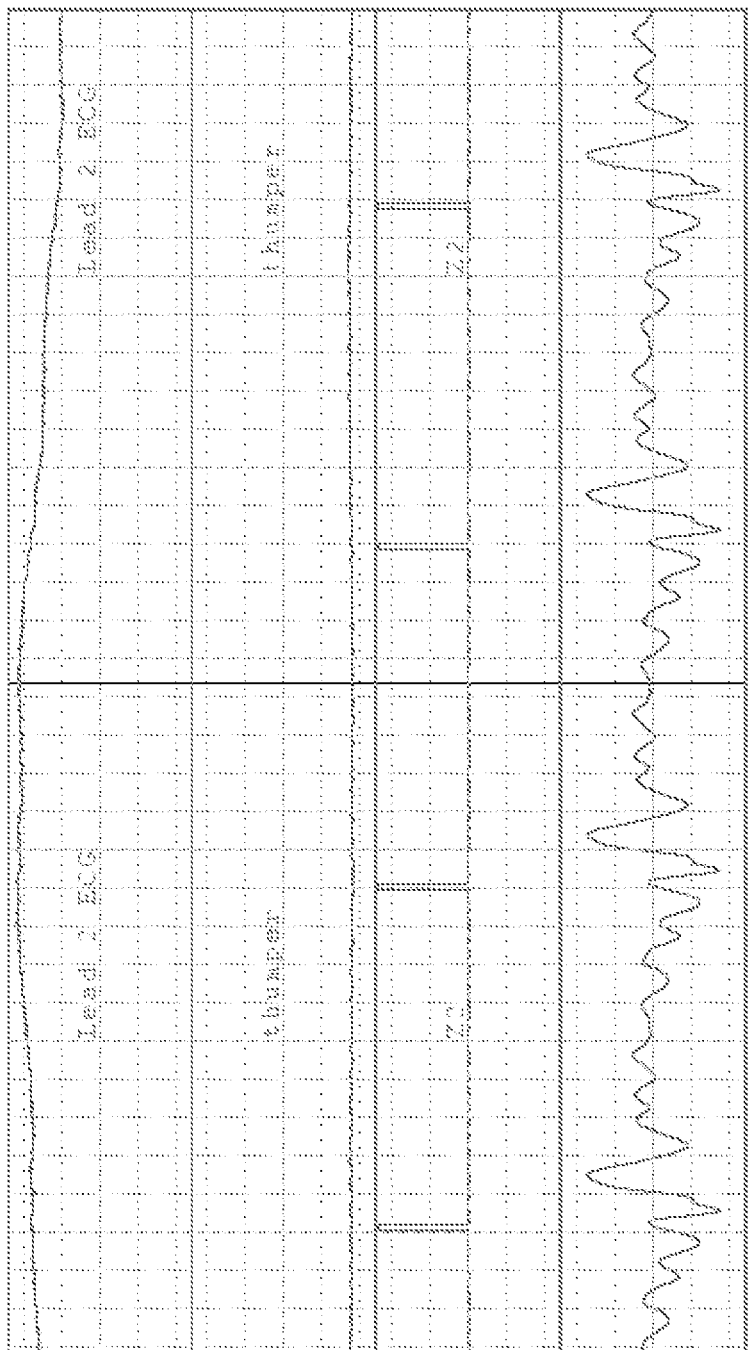
FIG. 24 is an expanded view of the one portion of the signals illustrated in FIG. 19, according to the present invention.

The following protocol was used to collect animal data with the data acquisition system. Two animals were studied early in this project to provide preliminary data on the performance of the system. For these tests, only the ECG and UWB radar were available for data collection. This data was used to optimize the algorithms, refine the test procedures and validate the hardware modifications. Upon receipt of the impedance catheter and completion of the hardware modifications, two animals were studied using the complete UWBMR and invasive stroke volume measurement techniques.
  a. The animals were intubated with a cuffed endotracheal tube and ventilated with a pressure-controlled ventilator at 10-15 ml/kg/min with an air/oxygen mixture set to maintain an arterial oxygen level of 100-150 mmHg. Electrocardiogram lead II was monitored throughout the study. The animals were placed in dorsal recombancy. Hemostatic sheaths were placed for vascular access in the femoral vessels
  b. A lateral left ventriculogram will be recorded using fluoroscopy at baseline to calibrate the cardiac conductance catheter as shown in FIG. 22. MATLAB image processing methods are used to determine ejection fraction, and systolic and diastolic volumes. Intravenous contrast agent was injected into the left ventricle through the lumen in the high fidelity catheter. Then a 12-electrode cardiac conductance catheter was inserted into the left ventricle in a retrograde fashion. A balloon catheter was inserted into the left femoral vein and advanced into the inferior vena cava just below the right atrium.
  c. Cardiac hypovolemia was induced by inflating the vena cava balloon until the arterial blood pressure decreased to below 60 mmHg. Radar data was collected for 20 seconds prior to balloon inflation. The balloon was left inflated for 30 seconds and then deflated. The animal was allowed to recover for 5 minutes before the procedure was repeated. The procedure was repeated 3-5 times in each animal. FIG. 23 shows the data collected during a typical test run while FIG. 24 shows the same test run with the time scale expanded so that the details of the UWB radar sync and video outputs can be seen.

The empirical data produced via the laboratory testing with animals was juxtaposed and compared with data produced earlier using only the single cardiac chamber phantom to identify previously unknown issues in the system and method used for collecting and processing the data to produce an assessment of chamber volume. Based on this comparison, the algorithmic elements were further refined to cause the UWBMR to more accurately measure stroke volume.

Figure 25:
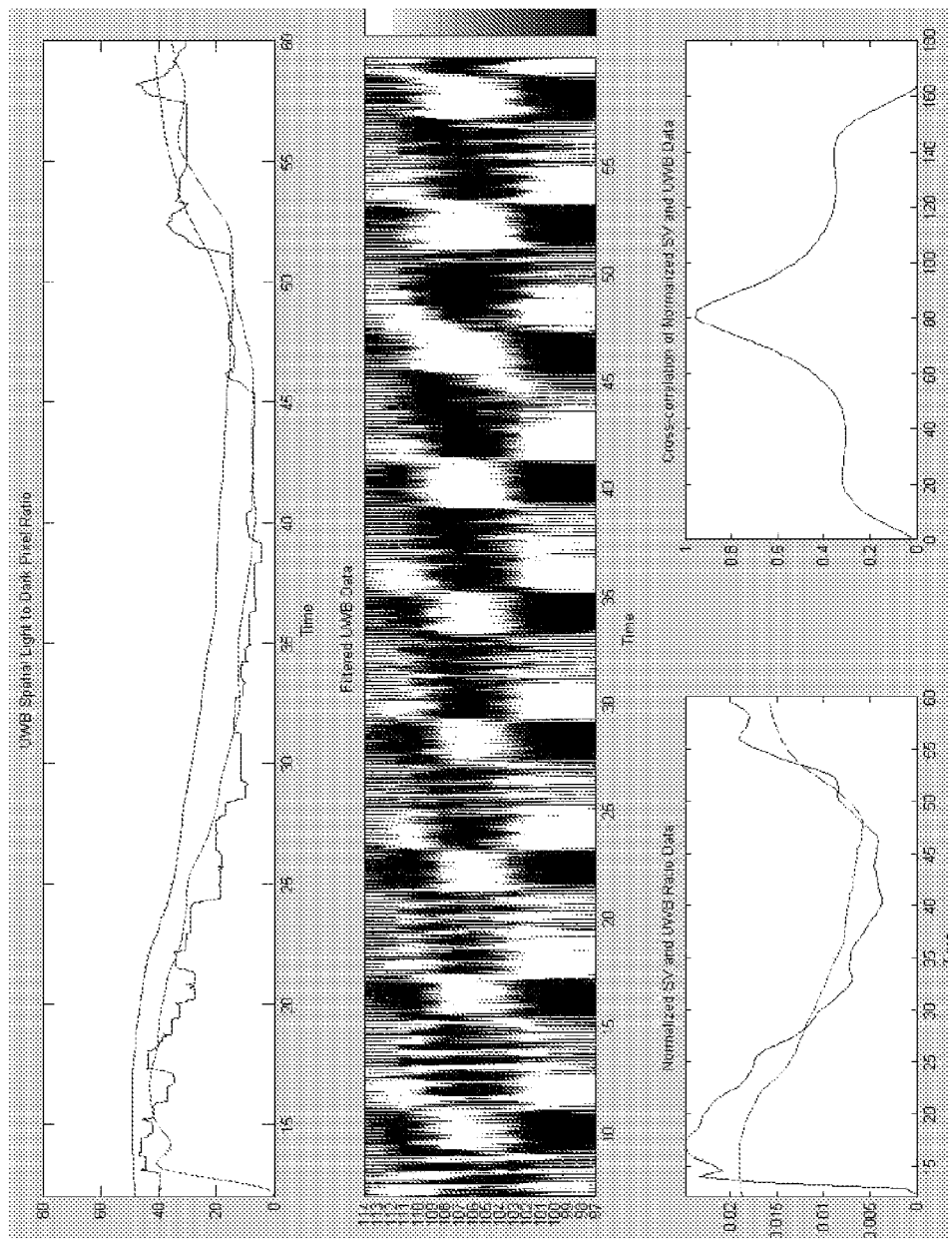
FIG. 25 is an illustration of the processed UWB data collected by the UWBMR sensor according to the present invention.

The collected animal data was post-processed using the novel algorithms developed and tested on the single chamber cardiac phantom. A software script was written to convert the raw impedance catheter data to stroke volume using the calibration data. Referring now to FIG. 25, the top pane shows three data plots of Stroke Volume for one of the test runs—impedance catheter (red), raw UWB machine vision (blue), and filtered UWB machine vision (green). As part of the basic algorithm, the raw UWB data is coarsely quantized by the machine vision algorithm, resulting in the high frequency stair-step noise noticeable in the blue plot. The data is subsequently smoothed with a 4-second moving average filter, which results in the smoother green plot. The lower left pane of FIG. 25 shows the normalized filtered UWB data and the impedance data together for comparison. The cross-correlation of the two data sets is shown in the lower right pane of FIG. 25.

Data generated using the refined UWBMR was determined to closely calibrate with data from the other methods used to confirm cardiac function, including the impedance data. Through the application of the advanced methods developed for the UWBMR, real-time determination of stroke volume using an external non-invasive UWBMR according to the present invention is shown to be a success.

The present invention can be incorporated with various handheld devices to provide a unique, mobile system for determining cardiac health, particularly as it applies to hemorrhagic events. Consequently, the present invention supports a unique implementation to support the development and fielding of a handheld device capable of accurately measuring cardiac stroke volume in the battlefield environment.

Figure 26:
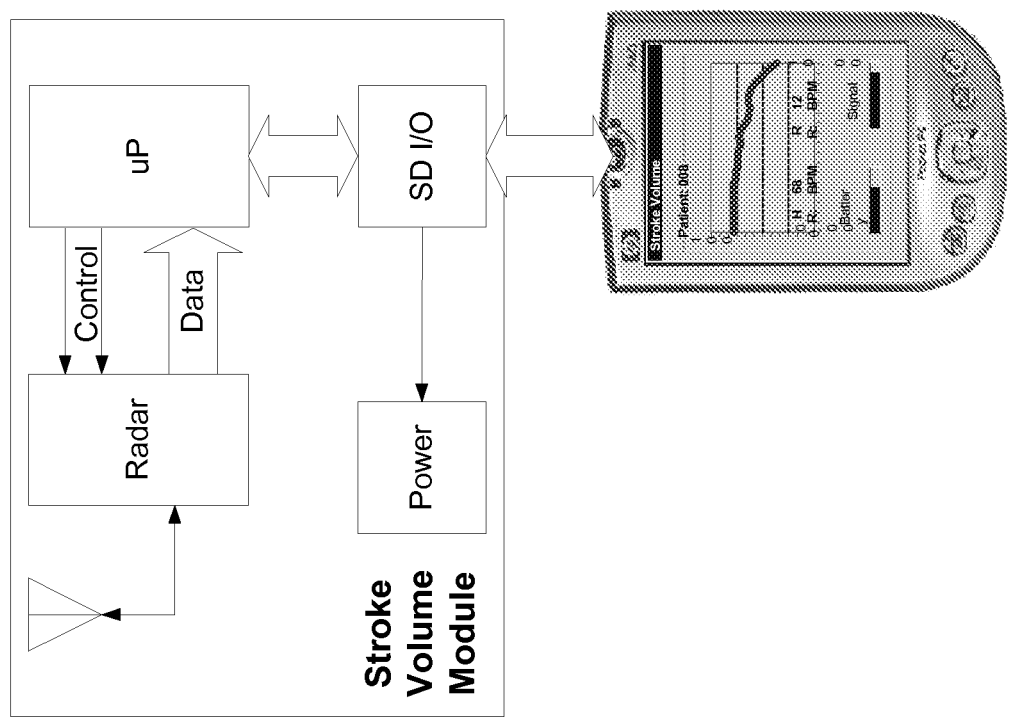
FIG. 26 is an illustration of the integration of an instantaneous chamber volume and stroke volume module with a typical PDA, according to the present invention.

As shown in FIG. 26, in one embodiment, the integrated device consists of a Portable Digital Assistant (PDA) and a Stroke Volume Module (SVM). This architecture allows a medic to use a single base device, the PDA, with a variety of dedicated modules for specific medical applications.

The SVM will connect to the PDA through the expansion bus port on the PDA. The expansion bus port is an industry standard input/output interface that allows compliant devices to work with the PDA. To minimize processor loading on the PDA, the Stroke Volume Module will contain a dedicated embedded processor responsible for controlling the UWB radar and processing the received data.

The present invention supports the deployment of a low-cost sensor based upon the UWBMR having a CPU with advanced software capable of displaying cardiac function results to a user.

The UWBMR demonstrates the viability of employing ultrawideband radar to detect conditions within the heart that will lead to a determination of changes in chamber volume. The method associated with the development of the device was comprised of several phases: (1) a theoretical analysis of the UWBMR system and human chest, (2) development, modification and enhancements to simple and more complex cardiac phantoms to provide empirical data to support adjustments and modifications to the UWBMR hardware and algorithms, and (3) comparison and analysis of measurements from the UWBMR against an impedance measurement approach to provide further enhancement of the various hardware and software components of the UWBMR to deliver a device and method capable of noninvasively yet accurately measuring and tracking cardiac stroke volume and changes in stroke volume.

The single chamber cardiac (SCC) phantom proved extremely useful for evaluating the effectiveness of enhancements to the UWB radar system. The SCC phantom supported development of a number of advanced algorithms, specifically tailored to the UWBMR purposes. The value of the use of a multi-element array has been confirmed.

Finally, during laboratory tests, the UWBMR's ability to detect and quantify changes in stroke volume was conclusively confirmed against other known methods of tracking stroke volume. In all tested cases, the UWBMR results tracked the impedance results.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The present invention has been particularly shown and described with respect to certain preferred embodiments and features thereof. However, it should be readily apparent to those of ordinary skill in the art that various changes and modifications in form and detail may be made without departing from the spirit and scope of the inventions as set forth in the appended claims. The inventions illustratively disclosed herein may be practiced without any element which is not specifically disclosed herein.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

INDUSTRIAL APPLICABILITY

The present invention may be used in the medical industry to measure and monitor cardiac performance in a subject to determine and to assist in the assessment and diagnosis of various cardiac conditions. In particular, the present invention may be used in the medical industry to continuously and noninvasively measure cardiac chamber volume of a subject to determine stroke volume and other derivative metrics providing indications of cardiac health. The measurement of stroke volume and other advanced cardiac parameters like cardiac output and ejection fraction provide critical information on the health of the heart and cardiovascular system. The present invention, the UWBMR, demonstrates the capability to non-invasively detect and measure stroke volume. A miniature UWBMR system able to integrate with a PDA would be a powerful diagnostic tool for emergency medical teams or chaotic trauma care situations common to the battlefield.

I claim:

1. A method for determining changes in cardiac chamber volume in a body using an ultrawideband (UWB) medical radar transceiver, the UWB medical radar transceiver including a transmitter and a receiver and a signal processor including software elements and a central processing unit, the method comprising:
    (a) transmitting from said transceiver a series of electromagnetic pulses into a body such that said electromagnetic impulses encounter a boundary between different biological regions in the body and small amounts of incident energy from said electromagnetic pulses encountering the boundary are reflected back towards said receiver as raw reflections;
    (b) capturing said raw reflections and pre-processing them using said receiver wherein said receiver captures a plurality of said raw reflections using a high speed sample and hold circuit where capture time for a sample of said raw reflections is set equal to a round trip time of flight from said transmitter to one or more depth ranges of interest and back to said receiver;
    (c) integrating said plurality of sampled reflections from said depth ranges of interest to form an integrated signal;
    (d) filtering said integrated signal to minimize irrelevant high frequency noise so as to avoid corruption of desired data related to tracking instantaneous cardiac chamber volume;
    (e) amplifying said integrated signal and passing said signal through a low-pass filter to prevent signal aliasing prior to digitization;
    (f) collecting and integrating a predetermined number of reflections for a first range of interest
    (g) changing said receiver sample timing and capturing reflections from a next range of interest
    (h) repeating (a) through (g) until reflections from an entire range of interest across the cardiac chamber are collected;
    (i) continually repeating (h) to deliver an updated instantaneous measure of cardiac volumetric changes.

2. The method according to claim 1 wherein said boundaries within a target range of interest move with respect to placement of said transceiver's antenna, producing a complex series of time-varying reflections, and wherein said complex series of time-varying reflections are continually processed by said signal processor to extract information on the mechanical activity of the heart.

3. The method according to according to claim 2 wherein said signal processor and central processing unit provide calculation of cardiac chamber volume via the additional steps of:
    range aligning said reflections on sweep boundaries;
    said range-aligned reflections are passed through one or more filters to minimize low frequency noise and static clutter;
    amplifying and coarse quantitized resultant data associated with all anatomical motion in said range of interest, including cardiac and pulmonary motion, using a binary quantizer where the quantizer threshold for a given sweep or row is based on the median value of the resultant data set, resulting in an intermediate black and white image,
    further refining said intermediate image through the application of one or more 1-dimensional or 2-dimensional filters to remove random speckle noise and increase the sharpness of the image boundary edges, to improve accuracy of measurement of spatial changes in the target range of interest, thereby presenting an image space comprised of various spatial structures changing in time representing both heart wall motion and various noise sources including organs, bones, and stray radiofrequency emissions.

4. The method according to claim 3 wherein said data is further refined via the application of at least one additional metric to delineate and confirm that said spatial structures found in said image space are cardiac wall excursions.

5. The method according to claim 4 wherein said at least one additional metric is cardiac rate wherein the cardiac rate is integrated within said signal processor and is detected via application and processing of said electromagnetic signals, said signal processor calculating the cardiac rate via conversion of an entire swept image space to a predetermined frequency domain using an algorithm, wherein said algorithm identifies and isolates an image region of said entire swept image space containing a strongest cardiac signal, while simultaneously determining a range of depth containing said strongest cardiac signal, wherein said cardiac signal depth and said cardiac signal is used to determine one or more additional metrics.

6. The method according to claim 4 wherein said at least one additional metric is cardiac structure completeness comprising the identification and verification of completeness of a target cardiac structure as said target cardiac structure changes over time by evaluating sustained and rhythmic behavior of said target cardiac structure, wherein said signal processor and said central processing unit in conjunction with said software identifies qualifying signals for further analysis by capturing and prioritizing those said qualifying signals with respect to minimum discontinuities, wherein a conversion process includes a chain coding technique in conjunction with at least one structural morphological technique to minimize signal discontinuities caused by noise loss.

7. The method according to claim 4 wherein said at least one additional metric is the continual and repeated identification and tracking of an ellipsoid characteristic in said image space wherein said ellipsoid characteristic best characterizes the approximate motion of anterior and posterior cardiac walls through time, and, wherein a corollary component of said identification and tracking of said ellipsoid characteristic is the isolation and avoidance of signals having a non-ellipsoid characteristic, wherein said non-ellipsoid signals indicate the likely presence of a non-cardiac signal source.

8. The method according to claim 4 wherein said at least one additional metric is the development of a correlation between the time-domain characteristics of an isolated cardiac range bin identified by a first cardiac rate metric with points identified in said image space that represent minimum, maximum, and zero-crossing points of cardiac wall excursions in said image space as identified by a second and a third metric.

9. The method according to claim 3 wherein said data is further refined via the application of at least one additional metric to delineate and confirm that said spatial structures found in said image space are cardiac wall excursions and not caused by other signal sources, and wherein image regions that meet the requirements of said at least one additional metric are isolated and identified as qualifying candidates for further analysis wherein a likely image region providing a most probable representation of instantaneous cardiac volume is an image region having the strongest characteristic in said at least one additional metric.

10. The method according to claim 9 wherein said likely image region is chosen, minimum and maximum cardiac wall excursions are identified and quantified using prior data acquired and already available from assessment of at least one additional metric, and wherein actual chamber wall displacement is calculated using said minimum and maximum cardiac wall excursions by counting spatial pixels traversed from a minimum point to a maximum point of the cardiac waveform to determine a count of spatial pixels traversed and multiplying said count of pixels by a resolution of the data capture device.

11. The method according to claim 10 wherein instantaneous cardiac volume is determined by the additional step of applying presumed dimensions of the target cardiac chamber in conjunction with said minimum and maximum cardiac wall excursions to determine volumetric changes in the target heart chamber.

12. The method according to claim 11 wherein said presumed dimensions of the target cardiac chamber are represented by one or more different shapes, wherein said shapes determine accuracy of calculated chamber volume and derivative stroke volume.

13. The method according to claim 12 wherein one of said one or more different shapes is a simplified sphere.

14. The method according to claim 12 wherein one of said one or more different shapes is an asymmetric changing ellipsoid.

15. The method according to claim 12 wherein one of said one or more different shapes is the actual shape of the cardiac chamber as determined by other precursor imaging and sizing methods, including x-ray, magnetic resonance imaging, ultrasound, surgery or other similar methods capable of determining dimensions of the target cardiac chamber.

16. The method according to claim 12 further including the additional steps of determining one or more cardiac performance parameters.

17. The method according to claim 16 wherein one of said one or more cardiac performance parameters is stroke volume, said stroke volume calculated by taking a difference between a maximum chamber volume and a minimum chamber volume on a beat-by-beat basis.

18. The method according to claim 17 wherein another one of said one or more cardiac performance parameters is cardiac output, said cardiac output calculated by multiplying said stroke volume by the heart rate.

19. The method according to claim 17 wherein another one of said one or more cardiac performance parameters is ejection fraction, said ejection fraction calculated by dividing said stroke volume by a maximum chamber volume.

* * * * *